United States Patent [19]

Carlsson et al.

[11] 4,165,384
[45] Aug. 21, 1979

[54] AMIDE SUBSTITUTED PHENOXY PROPANOL AMINES

[75] Inventors: Enar I. Carlsson, Kungsbacka; Gustav B. R. Samuelsson, Mölnlycke; Axel K. G. Aberg, Asa station, all of Sweden

[73] Assignee: Aktiebolaget Hässle, Gothenburg, Sweden

[21] Appl. No.: 760,290

[22] Filed: Jan. 19, 1977

Related U.S. Application Data

[63] Continuation-in-part of Ser. No. 610,381, Sep. 4, 1975, abandoned.

[30] Foreign Application Priority Data

Nov. 4, 1974 [SE] Sweden .................. 7413789

[51] Int. Cl.$^2$ .......................... C07C 103/78
[52] U.S. Cl. .................. 424/324; 260/559 R; 260/559 A; 260/559 D; 260/559 P; 260/559 B; 260/566 AE; 260/570.7; 424/327; 424/330; 424/300; 424/248.54; 424/248.55; 424/248.51; 424/248.56
[58] Field of Search ........... 260/559 A, 559 D, 559 P, 260/559 B, 559 R, 570.8 R, 570.70 H; 424/324

[56] References Cited

U.S. PATENT DOCUMENTS

| | | | |
|---|---|---|---|
| 3,676,493 | 7/1972 | Smith .................. | 260/559 A |
| 3,723,524 | 3/1973 | Augstein et al. .......... | 260/555 S |
| 3,755,413 | 8/1973 | Koppe et al. ............ | 260/559 A |
| 3,845,123 | 10/1974 | Cox et al. .............. | 260/562 P |
| 3,911,008 | 10/1975 | Edinberry et al. ........ | 260/559 A |
| 3,949,088 | 4/1976 | Samualsson et al. ....... | 260/559 A |

FOREIGN PATENT DOCUMENTS 2357849 6/1974 Fed. Rep. of Germany ...... 260/559 A
1245148 9/1971 United Kingdom .

*Primary Examiner*—Arthur P. Demers
*Attorney, Agent, or Firm*—Brumbaugh, Graves, Donohue & Ramond

[57] ABSTRACT

An amine of the formula I set forth below

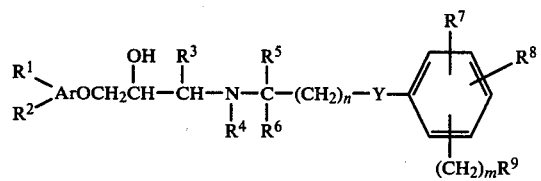

and a method for the preparation thereof and treating cardiovascular diseases to exert its α-receptor blocking activity.

6 Claims, No Drawings

AMIDE SUBSTITUTED PHENOXY PROPANOL AMINES

This application is a continuation-in-part of our co-pending application, Ser. No. 610,381, filed Sept. 4, 1975, now abandoned.

The present invention relates to new amines having β-receptor blocking activity and which are useful in treating cardiovascular diseases and have the general formula I

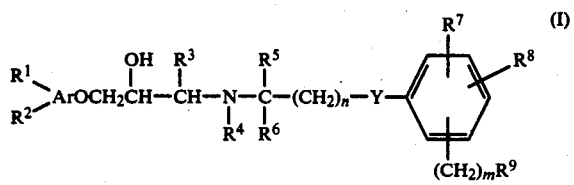

wherein $R^1$ is selected from the group consisting of —$CH_2CH=CH_2$, —$CH_2C\equiv CH$, —$OCH_2CH=CH_2$, —$OCH_2C\equiv CH$, alkyl, alkoxyalkyl, alkoxyalkoxy, alkoxycarbonylaminoalkyl, alkoxycarbonylaminoalkoxy, alkoxycarbonylaminoalkenyl, $HOCH_2CH_2NHCOCH_2O$—, $CH_3OCH_2CH_2NH$—$COCH_2O$—, and —CH=NOR, wherein R is selected from the group consisting of hydrogen and alkyl having 1 to 6 carbon atoms, $R^2$ is selected from the group consisting of hydrogen, halogen, alkyl, and alkoxy, $R^3$ is selected from the group consisting of hydrogen and alkyl, $R^4$ is selected from the group consisting of hydrogen, alkanoyl, and benzyl, $R^5$ and $R^6$ are each severally selected from the group consisting of hydrogen and alkyl, $R^7$ and $R^8$ are each severally selected from the group consisting of hydrogen, halogen, alkyl and alkoxy, $R^9$ is selected from the group consisting of hydrogen, alkanoyl, sulpho, sulphino, cyano, trifluoromethyl, alkoxycarbonylaminoalky, —$CHNR^{10}R^{11}$, and —$CONHNR^{10}R^{11}$ wherein $R^{10}$ and $R^{11}$ are hydrogen, or wherein $R^{10}$ and $R^{11}$ together with the nitrogen, to which they are bound, form a heterocyclic ring such as pyrrolidine, piperidine, piperazine, and morpholine, Y is selected from the group consisting of —O—, and —$CH_2$, n is an integer from 0 to 5, m is an integer from 0 to 2 and Ar is selected from the group consisting of phenyl, thiazolyl, or thiadiazolyl, whereby $R^1$ is bound in the 2 or 3 position to the phenyl, in 4 or 5 position to the thiazolyl, and $R^1$ or $R^2$ in the 4-position to the thiadiazolyl group, whereby when Y is $CH_2$, n is 1–5 when $R^1$ is methyl it is not bound in 2-position to the phenyl group, except when $R^9$ is alkoxycarbonylaminoalkyl, when $R^1$ is isobutyl in 3-position both $R^5$ and $R^6$ not being methyl, and when $R^1$ is acetylaminomethyl in 3-position m is not 0. Thiazolyl Ar is bound in the 2-position to the oxygen atom, whereby it carries $R^1$ and $R^2$ in 4 and 5 position, alternatively.

Thiadiazolyl Ar is 1,2,5-thiadiazolyl which is bound in the 3 position to the oxygen atom and carries $R^1$ or $R^2$ in the 4 position.

$R^5$ and $R^6$ may be the same or may be different.

$R^7$ and $R^8$ may be the same or may be different.

Alkyl $R^1$ has up to 7 carbon atoms, preferably up to 4 carbon atoms and is straight or branched- Alkyl $R^1$ is thus preferably methyl, ethyl, n-propyl, isopropyl, n-butyl, sec-butyl, or tert-butyl. Alkyl $R^1$ is not methyl in the 2-position on the phenyl nucleus.

Alkoxyalkyl $R^1$ has up to 7 carbon atoms in each alkyl chain, preferably up to 4 carbon atoms in each and each of them may be straight and/or branched. Alkoxyalkyl $R^1$ is thus e.g. methoxymethyl, methoxyethyl, ethoxyethyl, isopropoxyethyl, n-propoxymethyl, or t-butyloxymethyl.

Alkoxyalkoxy $R^1$ has up to 7 carbon atoms in each alkyl chain, preferably up to 4 carbon atoms in each, whereby each of them may be straight or branched. Alkoxyalkoxy $R^1$ is thus e.g. methoxymethoxy, methoxyethoxy, ethoxyethoxy, isopropoxyethoxy, 2-ethoxy-1-methylethoxy, or t-butoxyethoxy.

Alkoxycarbonylaminoalkyl $R^1$ has up to 7 carbon atoms, preferably up to 4 carbon atoms in the alkoxy group, which group is straight or branched and is for example methoxy, ethoxy or isopropoxy. The alkyl group has also up to 7 carbon atoms, preferably up to 4 carbon atoms, which group is straight or branched. Alkoxycarbonylaminoalkyl $R^1$ is e.g. thus methoxycarbonylaminomethyl, methoxycarbonylaminoethyl, 1-methyl-2-methoxycarbonylaminoethyl, isopropoxycarbonylaminoethyl or isopropoxycarbonylaminopropyl.

Alkoxycarbonylaminoalkoxy $R^1$ has in each alkoxy group up to 7 carbon atoms preferably up to 4 carbon atoms, which groups are straight or branched. Alkoxycarbonylaminoalkoxy $R^1$ is e.g. thus methoxycarbonylaminomethoxy, methoxycarbonylaminoethoxy, ethoxycarbonylaminoethoxy, isopropoxycarbonylaminoethoxy or isopropoxycarbonylaminopropoxy.

The alkoxy part of alkoxycarbonylaminoalkenyl $R^1$ has the same meaning as the alkoxy part of alkoxycarbonylaminoalkyl $R^1$ and is e.g. methoxy, ethoxy, or isopropoxy. The alkenyl part carrying the alkoxycarbonylamino part has up to 7 carbon atoms, preferably up to 4 carbon atoms and is straight or branched, and is e.g. ethenyl, allyl, 1-methylethenyl or 2-methylallyl. Alkoxycarbonylaminoalkenyl $R^1$ is thus e.g. methoxycarbonylaminoethenyl, ethoxycarbonylaminoallyl, or isopropoxycarbonylaminoallyl.

$R^1$ being —CH=NOR, wherein R is hydrogen, or alkyl with 1 to 6 carbon atoms is e.g. isonitrosomethyl, methylisonitrosomethyl, ethylisonitrosomethyl, n-propylisonitrosomethyl, isopropylisonitrosomethyl.

Halogen $R^2$ is e.g. chloro, fluoro or bromo.

Alkyl $R^2$ has up to 7 carbon atoms, preferably up to 4 carbon atoms, and is straight or branched and is e.g. methyl, ethyl, n-propyl, isopropyl, n-butyl, sec-butyl, tert-butyl.

Alkoxy $R^2$ has up to 7 carbon atoms preferably up to 4 carbon atoms and is straight or branched and is e.g. methoxy, ethoxy, n-propoxy, isopropoxy, n-butoxy, and t-butoxy.

Alkyl $R^3$ has the same meaning as alkyl $R^2$ and is e.g. methyl, ethyl, n-propyl, isopropyl, n-butyl, sec-butyl or t-butyl.

Alkanolyl $R^4$ has up to 7 carbon atoms preferably up to 4 carbon atoms, and is straight or branched, and is e.g. formyl, acetyl, propionyl, butyryl, isopropionyl, or sec-butyryl.

Alkyl $R^5$ and alkyl $R^6$ have the same meaning as alkyl $R^2$ and are e.g. methyl, ethyl, n-propyl, isopropyl, n-butyl, sec-butyl or t-butyl.

Halogen $R^7$ is e.g. chloro, fluoro or bromo.

Alkyl $R^7$ and alkyl $R^8$ have the same meaning as alkyl $R^2$ and are e.g. methyl, ethyl, propyl, isopropyl, n-butyl, sec-butyl or t-butyl.

Alkoxy $R^7$ and alkoxy $R^8$ have the same meaning as alkoxy $R^2$ and are e.g. methoxy, ethoxy, propoxy, isopropoxy, n-butoxy or t-butoxy.

Formyl $R^9$ is the group —(HCO).

Alkanoyl $R^9$ has the same meaning as alkanoyl $R^4$ and is e.g. acetyl, propionyl, n-butyryl or t-butyryl.

Sulpho $R^9$ is the group $HO_3S—$.

Sulphino $R^9$ is the group $HO_2S—$.

Cyano $R^9$ is the group $NC—$.

m is preferably 0 or 1.

n is preferably 1 or 2.

The new compounds have valuable pharmacological properties. Thus they block cardial $\beta$-receptors, which is shown in the determination of the inhibition of tachycardia after an intravenous injection of 0.5 μg/kg of d/l-isoproterenol sulphate in an anesthetized cat at an intravenous dose of 0.002 to 2 mg/kg. Thus they block the vascular $\beta$-receptors which is shown in the determination of the inhibition of vasodilation after an intravenous injection of 0.5 μg/kg of d/l-isopropterenol sulphate in an anesthetized cat at an intravenous dose of 3 mg/kg or more. They are thus heart selective.

The new compounds can be used as cardioselective antagonists of adrenergic $\beta$-receptor stimulators, e.g. in the treatment of exogenously or endogenously caused arrythmias and angina pectoris. One may also use them as intermediates in the preparation of other valuable pharmaceutical compounds.

Outstanding amines are also those of formula Ia

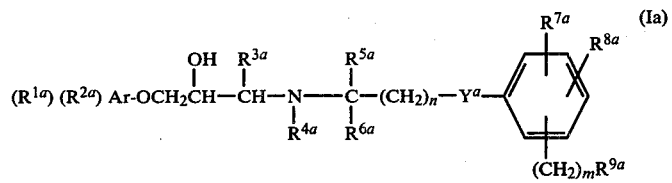

wherein $R^{1a}$ is selected from the group consisting of $—CH_2CH=CH_2$ and $—CH_2C≡CH$. $R^{2a}$ is selected from the group consisting of hydrogen, halogen, alkyl, and alkoxy, $R^{3a}$ is selected from the group consisting of hydrogen and alkyl, $R^{4a}$ is selected from the group consisting of hydrogen, alkanoyl, and benzyl, $R^{5a}$ and $R^{6a}$ are each selected from the group consisting of hydrogen, and alkyl $R^{7a}$ and $R^{8a}$ are each selected from the group consisting of hydrogen, halogen, alkyl, and alkoxy, $R^{9a}$ is selected from the group consisting of hydrogen, alkanoyl, sulpo, sulphino, cyano, trifluoromethyl, alkoxycarbonylaminoalkyl, $—CONR^{10a}R^{11a}$, and $—CONHNR^{10a}R^{11a}$, wherein $R^{10a}$ and $R^{11a}$ are hydrogen or wherein $R^{10a}$ and $R^{11a}$ together with the nitrogen atom to which they are bound form a heterocyclic ring, $Y^a$ is a divalent member selected from the group consisting of $—O—$, and $—CH_2—$, n is an integer from 0 to 5, m is an integer from 0 to 2, and Ar is phenyl, thiazolyl or thiadiazolyl, whereby when $Y^a$ is $CH_2$, n is 1-5, $R^{1a}$ is bound in 2 or 3 position to the phenyl, in the 4 or 5 position to the thiazolyl and in 4-position to the thiadiazolyl group, or a therapeutically acceptable salt thereof.

Of the compounds of the formula Ia, such compounds are especially advantageous, wherein $R^{1a}$ is $o—CH_2CH=CH_2$, $m—CH_2CH=CH_2$, $o—CH_2C≡CH$, or $m—CH_2C≡CH$, $R^{2a}$ is hydrogen, chloro, bromo, methyl, ethyl, methoxy or ethoxy, $R^{3a}$ is hydrogen or methyl, $R^{4a}$ is hydrogen, formyl, acetyl or benzyl, $R^{5a}$ and $R^{6a}$ are each hydrogen, methyl or ethyl, $R^{7a}$ and $R^{8a}$ are each hydrogen, chloro, bromo, methyl, ethyl, methoxy or ethoxy, $R^{9a}$ is hydrogen, formyl, acetyl, sulpho, sulphino, cyano, trifluoromethyl, methoxycarbonylaminoethyl, ethoxycarbonylaminoethyl, carbamoyl, methylcarbamyl, dimethylcarbamyl, morpholinecarbonyl, $Y^{1a}$ is $—O—$ or $—CH_2—$, n is an integer from 0 to 5, m is an integer from 0 to 2, Ar is phenyl or thiazolyl, whereby when $Y^a$ is $CH_2$, n is 1-5, and whereby $R^{1a}$ is bound in the 2 or 3 position to the phenyl and in the 4 or 5 position to the thiazolyl group, or a therapeutically acceptable salt thereof.

Preferably those compounds will be mentioned of formula Ia, wherein $R^{1a}$ is $o—CH_2CH=CH_2$ and $o—CH_2C≡CH$, $R^{2a}$ is hydrogen, chloro, methyl, and methoxy, $R^{3a}$ is hydrogen, $R^{4a}$ is hydrogen, $R^{5a}$ and $R^{6a}$ are each severally hydrogen or methyl, $R^{7a}$ and $R^{8a}$ are each severally hydrogen or methyl, $R^{9a}$ is hydrogen, carbamyl, methoxycarbonylaminoethyl, methylcarbamyl, morpholinecarbonyl, $Y^a$ is $—O—$, n is 1 or 2, m is 0, 1 or 2, Ar is phenyl, or a therapeutically acceptable salt thereof.

Outstanding amines are also those of the formula Ib

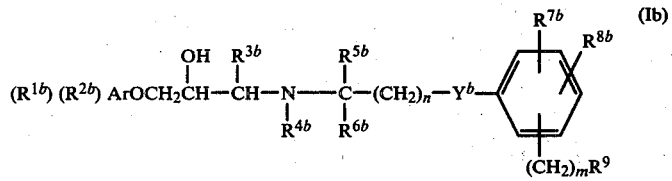

wherein $R^{1b}$ is selected from the group consisting of $—OCH_2CH=CH_2$ and $—OCH_2C≡CH$, $R^{2b}$ is selected from the group consisting of hydrogen, halogen, alkyl and alkoxy, $R^{3b}$ is selected from the group consisting of hydrogen and alkyl, $R^{4b}$ is selected from the group consisting of hydrogen, alkanoyl and benzyl, $R^{5b}$ and $R^{6b}$ are each selected from the group consisting of hydrogen, and alkyl, $R^{7b}$ and $R^{8b}$ are each selected from the group consisting of hydrogen, halogen, alkyl and alkoxy, $R^{9b}$ is selected from the group consisting of hydrogen, alkanoyl, sulpho, sulphino, cyano, trifluoromethyl, alkoxycarbonylaminoalkyl, $—CONR^{10b}R^{11b}$, and $—CONHNR^{10b}R^{11b}$, wherein $R^{10b}$ and $R^{11b}$ are hydrogen, or wherein $R^{10b}$ and $R^{11b}$ together with the nitrogen atom to which they are bound form a heterocyclic ring, $Y^b$ is a divalent member selected from the group consisting of $—O—$, and $—CH_2—$, n is an integer from 0 to 5, m is an integer from 0 to 2, and Ar is phenyl, thiazolyl- and thiadiazolyl, whereby $Y^b$ is —CH$_2$, n is 1-5, and whereby $R^1$ is bound in the 2 or 3 position to the phenyl, in the 4 or 5 position to the thiazolyl and in the 4 position to the thiadiazolyl group, or a therapeutically acceptable salt thereof.

Of the compounds of the formula Ib such compounds are especially advantageous, wherein $R^{1b}$ is —OCH$_2$CH=CH$_2$ or —OCH$_2$C≡CH, $R^{2b}$ is hydrogen, chloro, bromo, methyl, ethyl, methoxy, and ethoxy, $R^{3b}$ is hydrogen or methyl, $R^{4b}$ is hydrogen, formyl, acetyl or benzyl, $R^{5b}$ and $R^{6b}$ are each hydrogen, methyl or ethyl, $R^{7b}$ and $R^{8b}$ are each hydrogen, chloro, bromo, methyl, ethyl, methoxy or ethoxy, $R^{9b}$ is hydrogen, formyl, acetyl, sulpho, sulphino, cyano, trifluoromethyl, methoxycarbonylaminoethyl, ethoxycarbonylaminoethyl, carbamyl, methylcarbamyl, dimethylcarbamyl, morpholinecarbonyl, $Y^b$ is —O—, and CH$_2$, n is an integer from 0 to 5, m is an integer from 0 to 2, Ar is phenyl or thiazolyl, whereby when $Y^b$ is CH$_2$, n is 1-5, and whereby $R^{1b}$ is bound in the 2 or 3 position to the phenyl- and in the 4 or 5 position to the thiazolyl group, or a therapeutically acceptable salt thereof.

Preferably those compounds will be mentioned of formula Ib, wherein $R^{1b}$ is o—OCH$_2$CH=CH$_2$ or o—OCH$_2$C≡CH, $R^{2b}$ is hydrogen, chloro, methyl or methoxy, $R^{3b}$ is hydrogen, $R^{4b}$ is hydrogen, $R^{5b}$ and $R^{6b}$ are each severally hydrogen or methyl, $R^{7b}$ and $R^{8b}$ are each severally hydrogen or methyl, $R^{9b}$ is hydrogen, carbamyl, methoxycarbonylaminoethyl, methylcarbamyl, morpholinecarbonyl, $Y^b$ is —O—, n is 1 or 2, m is 0, 1 or 2, Ar is phenyl, or a therapeutically acceptable salt thereof.

Outstanding amines are also those of formula Ic from 0-2 and Ar is phenyl, thiazolyl or thiadiazolyl, whereby when $Y^c$ is —CH$_2$— n is 1-5, and whereby $R^{1c}$ is bound in the 2 or 3 position to the phenyl, in the 4 or 5 position to the thiazolyl and in the 4 position to the thiadiazolyl group, whereby when $R^{1c}$ is methyl it is not bound in the 2 position to the phenyl, except when $R^{9c}$ is alkoxycarbonylaminoalkyl and when $R^{1c}$ is isobutyl both $R^{5c}$ and $R^{6c}$ not being methyl.

Of the compounds of the formula Ic such compounds are especially advantageous, wherein $R^{1c}$ is alkyl or alkoxyalkyl, $R^{2c}$ is hydrogen, chloro, bromo, methyl, ethyl, methoxy or ethoxy, $R^{3c}$ is hydrogen or methyl, $R^{4c}$ is hydrogen, formyl, acetyl, or benzyl, $R^{5c}$ and $R^{6c}$ are each hydrogen, methyl or ethyl, $R^{7c}$ and $R^{8c}$ are each hydrogen, chloro, bromo, methyl, ethyl, methoxy or ethoxy, $R^{9c}$ is hydrogen, formyl, acetyl, sulpho, sulphino, cyano, trifluoromethyl, methoxycarbonylaminoethyl, ethoxycarbonylaminoethyl, carbamyl, methylcarbamyl, dimethylcarbamyl, morpholinecarbonyl, $Y^c$ is —O—, or —CH$_2$, n is an integer from 0 to 5, m is an integer from 0 to 2, Ar is phenyl or thiazolyl, whereby when $Y^c$ is CH$_2$, n is 1-5, and whereby $R^{1c}$ is bound in the 2 or 3 position to the phenyl- and in 4 or 5 position to the thiazolyl group.

Preferably those compounds will be mentioned of formula Ic, wherein $R^{1c}$ is methyl, ethyl, methoxymethyl, methoxyethyl, or ethoxyethyl, $R^{2c}$ is hydrogen, chloro, methyl and methoxy, $R^{3c}$ is hydrogen, $R^{4c}$ is hydrogen, $R^{5c}$ and $R^{6c}$ are each severally hydrogen or methyl, $R^{7c}$ and $R^{8c}$ are each severally hydrogen or methyl, $R^{9c}$ is hydrogen, carbamyl, methoxycarbonylaminoethyl, methylcarbamyl, morpholinecarbonyl, $Y^c$ is —O—, n is 1 or 2, m is 0, 1 or 2, Ar is phenyl or therapeutically acceptable salts thereof.

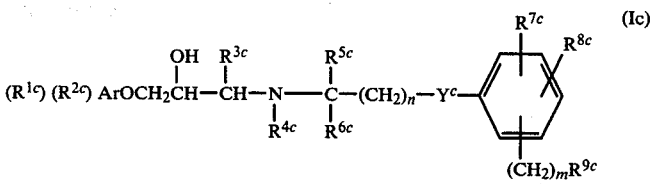

(Ic)

wherein $R^{1c}$ is selected from the group consisting of alkyl and alkoxyalkyl, $R^{2c}$ is selected from the group consisting of hydrogen, halogen, alkyl, and alkoxy, $R^{3c}$ is selected from the group consisting of hydrogen and alkyl, $R^{4c}$ and $R^{6c}$ are each selected from the group consisting of hydrogen and alkyl, $R^{7c}$ and $R^{8c}$ are each selected from the group consisting of hydrogen, halogen, alkyl and alkoxy, $R^{9c}$ is selected from the group consisting of hydrogen, alkanoyl, sulpho, sulphino, cyano, trifluoromethyl, alkoxycarbonylaminoalkyl, —CONR$^{10c}$R$^{11c}$, and —CONHNR$^{10c}$R$^{11c}$, wherein R$^{10c}$ and R$^{11c}$ are hydrogen or wherein R$^{10c}$ and R$^{11c}$ together with the nitrogen atom to which they are bound form a heterocyclic ring, $Y^c$ is a divalent member selected from the group consisting of —O—, and —CH$_2$—, n is an integer from 0 to 5, m is an integer Outstanding amines are also those of formula Id

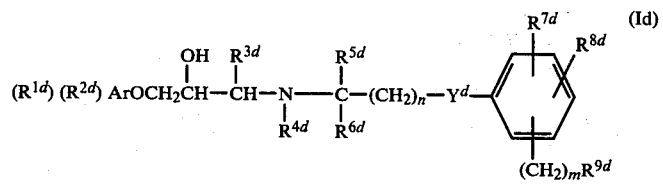

(Id)

wherein $R^{1d}$ is alkoxyalkoxy, $R^{2d}$ is selected from the group consisting of hydrogen, halogen, alkyl and alkoxy, $R^{3d}$ is selected from the group consisting of hydrogen and alkyl, $R^{4d}$ is selected from the group consisting of hydrogen, alkanoyl, and benzyl, $R^{5d}$ and $R^{6d}$ are each selected from the group consisting of hydrogen and alkyl, $R^{7d}$ and $R^{8d}$ are each selected from the group consisting of hydrogen, halogen, alkyl and alkoxy, $R^{9d}$ is selected from the group consisting of hydrogen, alkanoyl, sulpho, sulphino, cyano, trifluoromethyl, alkoxycarbonylaminoalkyl, —CONR$^{10d}$R$^{11d}$, and —CONHNR$^{10d}$R$^{11d}$, wherein R$^{11d}$ are hydrogen or wherein R$^{10d}$ and R$^{11d}$ together with the nitrogen atom to which they are bound form a heterocyclic ring, $Y^d$ is a divalent member selected from the group consisting of —O—, and —CH$_2$—, n is an integer from 0 to 5, m is an integer from 0 to 2 and Ar is phenyl, thiazolyl, or thiadiazolyl, whereby R$^{1d}$ is bound in 2 or 3 position to the phenyl, in 4 or 5 position to the thiazolyl, and in 4 position to the thiadiazolyl group, whereby when Y$^d$ is —CH$_2$—, n is 1-5.

Of the compounds of the formula Id such compounds are especially advantageous, wherein R$^{1d}$ is alkoxyalkoxy, R$^{2d}$ is hydrogen, chloro, bromo, methyl, ethyl, methoxy and ethoxy, R$^{3d}$ is hydrogen or methyl, R$^{4d}$ is hydrogen, formyl, acetyl or benzyl, R$^{5d}$ and R$^{6d}$ are each hydrogen, methyl or ethyl, R$^{7d}$ and R$^{8d}$ are each hydrogen, chloro, bromo, methyl, ethyl, methoxy or ethoxy, R$^{9d}$ is hydrogen, formyl, acetyl, sulpho, sulphino, cyano, trifluoromethyl, methoxycarbonylaminoethyl, ethoxycarbonylaminoethyl, carbamyl, methylcarbamyl, dimethyl, carbamyl, morpholinecarbonyl, Y$^d$ is —O—, or —CH$_2$—, n is an integer from 0 to 5, m is an integer from 0 to 2, Ar is phenyl or thiazolyl, whereby when Y$^d$ is CH$_2$, n is 1-5, whereby R$^{1d}$ is bound in the 2 or 3 position to the phenyl and in 4 or 5 position to the thiazolyl group, or a therapeutically acceptable salt thereof.

Preferably those compounds will be mentioned of formula Id, wherein R$^{1d}$ is methoxymethoxy, methoxyethoxy or ethoxyethoxy, R$^{2d}$ is hydrogen, chloro, methyl or methoxy, R$^{3d}$ is hydrogen, R$^{4d}$ is hydrogen, R$^{5d}$ and R$^{6d}$ are each severally hydrogen or methyl, R$^{7d}$ and R$^{8d}$ are each severally hydrogen or methyl, R$^{9d}$ is hydrogen, carbamyl, methoxycarbonylaminoethyl, methylcarbamyl, morpholinecarbonyl, Y$^d$ is —O—, n is 1 or 2, m is 0, 1 or 2, Ar is phenyl, or a therapeutically acceptable salt thereof.

Outstanding amines are also those according to formula Ig gen or wherein R$^{10g}$ and R$^{11g}$ together with the nitrogen atom to which they are bound form a heterocyclic ring, Y$^g$ is a divalent member selected from the group consisting of —O—, and —CH$_2$—, n is an integer from 0 to 5, m is an integer from 0 to 2, and Ar is phenyl, thiazolyl or thiadiazolyl, whereby R$^{1g}$ is bound in 2 or 3 position to the phenyl, in 4 or 5 position to the thiazolyl, and in the 4 position to the thiadiazolyl group, whereby when Y$^g$ is —CH$_2$—, n is 1-5.

Of the compounds of the formula Ig such compounds are especially advantageous, wherein R$^{1g}$ is alkoxycarbonylaminoalkoxy, HOCH$_2$CH$_2$NHCOCH$_2$O— or CH$_3$OCH$_2$NHCOCH$_2$O—, R$^{2g}$ is hydrogen, chloro, bromo, methyl, ethyl, methoxy and ethoxy, R$^{3g}$ is hydrogen or methyl, R$^{4g}$ is hydrogen, formyl, acetyl or benzyl, R$^{5g}$ and R$^{6g}$ are each hydrogen, methyl or ethyl, R$^{7g}$ and R$^{8g}$ are each hydrogen, chloro, bromo, methyl, ethyl, methoxy or ethoxy, R$^{9g}$ is hydrogen, formyl, acetyl, sulpho, sulphino, cyano, trifluoromethyl, methoxycarbonylaminoethyl, ethoxycarbonylaminoethyl, carbamyl, methylcarbamyl, dimethylcarbamyl, morpholinecarbonyl, Y$^g$ is —O— or —CH$_2$—, n is an integer from 0 to 5, m is an integer from 0 to 2, Ar is phenyl or 2-thiazolyl, whereby when Y$^g$ is CH$_2$, n is 1-2, and whereby R$^{1g}$ is bound in the 2 or 3 position to the phenyl and in the 4 or 5 position to the thiazolyl group, or a therapeutically acceptable salt thereof.

Preferably those compounds will be mentioned according to formula I$_g$, wherein R$^{1g}$ is methoxycarbonylaminoethoxy, methoxycarbonylaminoethoxy, ethoxycarbonylaminoethoxy, ethoxycarbonylaminomethoxy, HOCH$_2$CH$_2$NHCOCH$_2$O— or CH$_3$OCH$_2$CH$_2$NHCOCH$_2$O—, R$^{2g}$ is hydrogen, chloro, methyl or methoxy, R$^{3g}$ is hydrogen, R$^{4g}$ is hydrogen, R$^{5g}$ and R$^{6g}$ are each severally hydrogen, hydroxy or methyl, R$^{7g}$ and R$^{8g}$ are each severally hy-

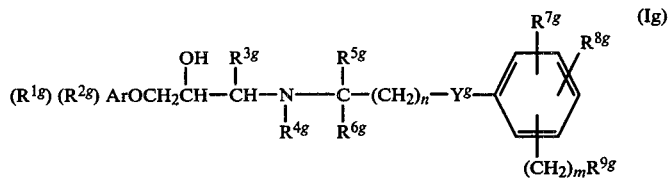

(Ig)

wherein R$^{1g}$ is selected from the group consisting of alkoxycarbonylaminoalkoxy, HOCH$_2$CH$_2$NHCOCH$_2$O— and CH$_3$OCH$_2$NHCOCH$_2$O—, R$^{2g}$ is selected from the group consisting of hydrogen, halogen, alkyl and alkoxy, R$^{3g}$ is selected from the group consisting of hydrogen and alkyl and R$^{4g}$ is selected from the group consisting of hydrogen, alkanoyl, and benzyl, R$^{5g}$ and R$^{6g}$ are each selected from the group consisting of hydrogen, and alkyl, R$^{7g}$ and R$^{8g}$ are each selected from the group consisting of hydrogen, halogen, alkyl and alkoxy, R$^{9g}$ is selected from the group consisting of hydrogen, alkanoyl, sulpho, sulphino, cyano, trifluoromethyl, alkoxycarbonylaminoalkyl, —CONR$^{10g}$R$^{11g}$, —CONHNR$^{10g}$R$^{11g}$, wherein R$^{10g}$ and R$^{11g}$ are hydrodrogen or methyl, R$^{9g}$ is hydrogen, carbamyl, methoxycarbonylaminoethyl, methylcarbamyl, morpholinecarbonyl, Y$^g$ is —O—, n is 1 or 2, m is 0, 1 or 2, Ar is phenyl, or a therapeutically acceptable salts thereof.

Outstanding amines are also those according to formula Ih

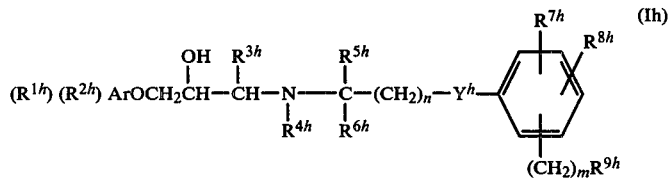

(Ih)

wherein R$^{1h}$ is selected from the group consisting of alkoxycarbonylaminoalkyl, R$^{2h}$ is selected from the group consisting of hydrogen, halogen, alkyl, and alkoxy, R$^{3h}$ is selected from the group consisting of hydrogen and alkyl, R$^{4h}$ is selected from the group consisting of hydrogen, alkanoyl, and benzyl, R$^{5h}$ and R$^{6h}$ are each selected from the group consisting of hydrogen, and alkyl, $R^{7h}$ and $R^{8h}$ are each selected from the group consisting of hydrogen, halogen, alkyl, and alkoxy, $R^{9h}$ is selected from the group consisting of hydrogen, alkanoyl, sulpho, sulphino, cyano, trifluoromethyl, alkoxycarbonylaminoalkyl, —$CONR^{10h}R^{11h}$ and —$CONHNR^{10h}R^{11h}$, wherein $R^{10h}$ and $R^{11h}$ are hydrogen or wherein $R^{10h}$ and $R^{11h}$ together with the nitrogen atom to which they are bound form a heterocyclic ring, $Y^h$ is a divalent member selected from the group consisting of —O— and —$CH_2$—, n is an integer from 0 to 5, m is an integer from 0 to 2 and Ar is phenyl, thiazolyl or thiadiazolyl, whereby $R^{1h}$ is bound in the 2 or 3 position to the phenyl, in the 4 or 5 position to the thiazolyl and in the 4 position to the thiadiazolyl group, whereby when $Y^h$ is —$CH_2$—, n is 1-5, and when $R^1$ is acetylaminomethyl in the 3 position, m is not 0.

Of the compounds of the formula Ih such compounds are especially advantageous, wherein $R^{1h}$ is alkoxycarbonylaminoalkyl, $R^{2h}$ is hydrogen, chloro, bromo, methyl, ethyl, methoxy, or ethoxy, $R^{3h}$ is hydrogen or methyl, $R^{4h}$ is hydrogen, formyl, acetyl, or benzyl, $R^{5h}$ and $R^{6h}$ are each hydrogen, methyl, or ethyl, $R^{7h}$ and $R^{8h}$ are each hydrogen, chloro, bromo, methyl, ethyl, methoxy, or ethoxy, $R^{9h}$ is hydrogen, formyl, acetyl, sulpho, sulphino, cyano, trifluoromethyl, methoxycarbonylaminoethyl, ethoxycarbonylaminoethyl, carbamyl, methylcarbamyl, dimethylcarbamyl or morpholinecarbonyl, $Y^h$ is —O— or —$CH_2$—, n is an integer from 0 to 5, m is an integer from 0 to 2, Ar is phenyl or thiazolyl, whereby when $Y^h$ is $CH_2$, n is 1-5, and whereby $R^{1h}$ is bound in the 2 or 3 position to the phenyl and in the 4 or 5 position to the thiazolyl group, or a therapeutically acceptable salt thereof.

Preferably those compounds will be mentioned according to formula Ih, wherein $R^{1h}$ is methoxycarbonylaminomethyl, methoxycarbonylaminoethyl, ethoxycarbonylaminoethyl, $R^{2h}$ is hydrogen, chloro, methyl or methoxy, $R^{3h}$ is hydrogen, $R^{4h}$ is hydrogen, $R^{5h}$ and $R^{6h}$ are each severally hydrogen or methyl, $R^{7h}$ and $R^{8h}$ are each severally hydrogen or methyl, $R^{9h}$ is hydrogen, carbamyl, methoxycarbonylaminoethyl, methylcarbamyl, morpholinecarbonyl, $Y^h$ is —O—, n is 1 or 2, m is 0, 1 or 2, Ar is phenyl, or a therapeutically acceptable salt thereof.

Outstanding amines are also those according to formula Ii group consisting of hydrogen, alkanoyl and benzyl, $R^{5i}$ and $R^{6i}$ are each selected from the group consisting of hydrogen, and alkyl, $R^{7i}$ and $R^{8i}$ are each selected from the group consisting of hydrogen, halogen, alkyl, and alkoxy, $R^{9i}$ is selected from the group consisting of hydrogen, alkanoyl, sulpho, sulphino, cyano, trifluoromethyl, alkoxycarbonylaminoalkyl, —$CONR^{10i}R^{11i}$, and —$CONHNR^{10i}R^{11i}$, wherein $R^{10i}$ and $R^{11i}$ are hydrogen or wherein $R^{10i}$ and $R^{11i}$ together with the nitrogen atom to which they are bound form a heterocyclic ring, $Y^i$ is a divalent member selected from the group consisting of —O— and —$CH_2$—, n is an integer from 0 to 5, m is an integer from 0 to 2 and Ar is phenyl, thiazolyl, or thiadiazolyl, whereby $R^{1i}$ is bound in the 2 or 3 position to the phenyl, in the 4 or 5 position to the thiazolyl, and in the 4 position to the thiadiazolyl, whereby when $Y^i$ is —$CH_2$—, n is 1-5.

Of the compounds of the formula Ii such compounds are especially advantageous, wherein $R^{1i}$ is alkoxycarbonylaminoalkenyl, $R^{2i}$ is hydrogen, chloro, bromo, methyl, ethyl, methoxy, or ethoxy, $R^{3i}$ is hydrogen or methyl, $R^{4i}$ is hydrogen, formyl, acetyl, or benzyl, $R^{5i}$ and $R^{6i}$ are each hydrogen, methyl, or ethyl, $R^{7i}$ and $R^{8i}$ are each hydrogen, chloro, bromo, methyl, ethyl, methoxy or ethoxy, $R^{9i}$ is hydrogen, formyl, acetyl, sulpho, sulphino, cyano, trifluoromethyl, methoxycarbonylaminoethyl, ethoxycarbonylaminoethyl, carbamyl, methylcarbamyl, dimethylcarbamyl, morpholinecarbonyl, $Y^i$ is —O— or —$CH_2$—, n is an integer from 0 to 5, m is an integer from 0 to 2, Ar is phenyl, thiazolyl, whereby when $Y^i$ is $Ch_2$, n is 1-5, and whereby $R^{1i}$ is bound in the 2 or 3 position to the phenyl and in the 4 or 5 position to the thiazolyl group, or a therapeutically acceptable salt thereof.

Preferably those compounds will be mentioned according to formula Ii, wherein $R^{1i}$ is methoxycarbonylaminoethenyl, methoxycarbonylaminoallyl, ethoxycarbonylaminoethenyl or ethoxycarbonylaminoallyl, $R^{2i}$ is hydrogen, chloro, methyl or methoxy, $R^{3i}$ is hydrogen, $R^{4i}$ is hydrogen, $R^{5i}$ and $R^{6i}$ are severally hydrogen or methyl, $R^{7i}$ and $R^{8i}$ are each severally hydrogen, or methyl, $R^{9i}$ is hydrogen, carbamyl, methoxycarbonylaminoethyl, methylcarbamyl, morpholinecarbonyl, $Y^i$ is —O—, n is 1 or 2, m is 0, 1 or 2, Ar is phenyl or a therapeutically acceptable salt thereof.

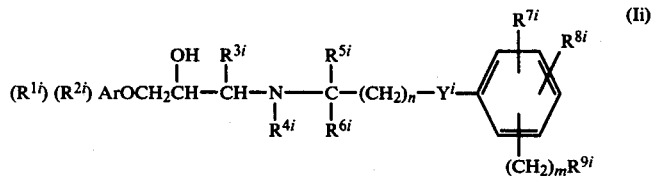
(Ii)

wherein $R^{1i}$ is alkoxycarbonylaminoalkenyl, $R^{2i}$ is selected from the group consisting of hydrogen, halogen, alkyl, and alkoxy, $R^{3i}$ is selected from the group consisting of hydrogen and alkyl, $R^{4i}$ is selected from the Outstanding amines are also those according to formula Ik

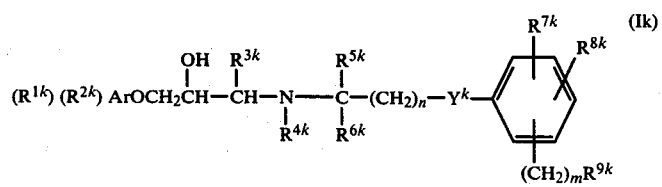
(Ik)

wherein $R^{1k}$ is —CH=NOR, wherein R is selected from the group consisting of hydrogen and alkyl having 1 to 6 carbon atoms, $R^{2k}$ is selected from the group consisting of hydrogen, halogen, alkyl, and alkoxy, $R^{3k}$ is selected from the group consisting of hydrogen and alkyl, $R^{4k}$ is selected from the group consisting of hydrogen, alkanoyl, and benzyl, $R^{5k}$ and $R^{6k}$ are each selected from the group consisting of hydrogen, and alkyl, $R^{7k}$ and $R^{8k}$ are each selected from the group consisting of hydrogen, halogen, alkyl, and alkoxy, $R^{9k}$ is selected from the group consisting of hydrogen, alkanoyl, sulpho, sulphino, cyano, trifluoromethyl, alkoxycarbonylaminoalkyl, —$CONR^{10k}R^{11k}$, and —$CONHNR^{10k}R^{11k}$, wherein $R^{10k}$ and $R^{11k}$ are hydrogen, or wherein $R^{10k}$ and $R^{11k}$ together with the nitrogen atom to which they are bound form a heterocyclic ring, $Y^k$ is a divalent member selected from the group consisting of —O— and —$CH_2$, n is an integer from 0 to 5, m is an integer from 0 to 2, and Ar is phenyl, thiazolyl or thiadiazolyl whereby $R^{1k}$ is bound in the 2 or 3 position to the phenyl, in the 4 or 5 position to the thiazolyl and in 4 position to the thiadiazolyl group, whereby when $Y^k$ is —$CH_2$—, n is 1–5.

Of the compounds of the formula Ik such compounds are especially advantageous, wherein $R^{1k}$ is —CH= NOR, wherein $R^k$ is hydrogen or alkyl having 1 to 6 carbon atoms, $R^{2k}$ is hydrogen, chloro, bromo, methyl, ethyl, methoxy, and ethoxy, $R^{3k}$ is hydrogen or methyl, $R^{4k}$ is hydrogen, formyl, acetyl, or benzyl, $R^{5k}$ and $R^{6k}$ are each hydrogen, methyl, or ethyl, $R^{7k}$ and $R^{8k}$ are each hydrogen, chloro, bromo, methyl, ethyl, methoxy, or ethoxy, $R^{9k}$ is hydrogen, formyl, acetyl, sulpho, sulphino, cyano trifluoromethyl, methoxycarbonyl, aminoethyl, ethoxycarbonylaminoethyl, carbamyl, methylcarbamyl, dimethylcarbamyl, morpholinecarbonyl, $Y^k$ is —O— or —$CH_2$—, n is an integer from 0 to 5, m is an integer from 0 to 2, Ar is phenyl or thiazolyl, whereby when $Y^k$ is $CH_2$, n is 1–5 and whereby $R^{1k}$ is bound in the 2 or 3 position to the phenyl and in the 2 position to the thiazolyl group, or a therapeutically acceptable salt thereof.

Preferably those compounds will be mentioned according to formula Ik, wherein $R^{1k}$ is isonitroso methyl, methylisonitrosomethyl, ethylisonitrosomethyl, propylisonitrosomethyl, or t-butylisonitrosomethyl, $R^{2k}$ is hydrogen, chloro, methyl or methoxy, $R^{3k}$ is hydrogen, $R^{4k}$ is hydrogen, $R^{5k}$ and $R^{6k}$ are each severally hydrogen or methyl, $R^{7k}$ and $R^{8k}$ are each severally hydrogen, or methyl, $R^{9k}$ is hydrogen, carbamyl, methoxycarbonylaminoethyl, methylcarbamyl, morpholinocarbonyl, $Y^k$ is —O—, n is 1 or 2, m is 0, 1 or 2, Ar is phenyl, or a therapeutically acceptable salt thereof.

The following compounds are especially mentioned
(1) 1-[2-(4-carbamylphenoxy)ethylamino]-3-(2-allylphenoxy)propanol-2.
(2) 1-[2-(4-carbamylphenoxy)ethylamino]-3-(2-chloro-5-methylphenoxy)propanol-2-.
(3) 1-[2-(4-carbamylphenoxy)ethylamino]-3-(2-methoxyethylphenoxy)propanol-2.
(4) 1-[2-(4-carbamylphenoxy)ethylamino]-3-(4-chloro-3-thiazoloxy)propanol-2.
(5) 1-[1-methyl-2-(4-carbamylphenoxy)ethylamino]-3-(2-allylphenoxy)propanol-2.
(6) 1-[1-methyl-2-(2-methylphenoxy)ethylamino]-3-(2-allylphenoxy)propanol-2.
(7) 1-[1-methyl-2-(4-methylphenoxy)ethylamino]-3-(2-allylphenoxy)propanol-2.
(8) 1-[2-(4-methoxycarbonylaminoethylphenoxy)ethylamino]-3-(2-methoxycarbonylaminoethylphenoxy)propanol-2.
(9) 1-[1-methyl-2-(4-methylcarbamylphenoxy)ethylamino]-3-(2-carbamylethylphenoxy)propanol-2.
(10) 1-[2-(2-trifluoromethylphenylamino)ethylamino]-3-(3-methylcarbonylaminoethylphenoxy)propanol-2.
(11) 1-[2-(4-carbamylethylphenoxy)ethylamino]-3-(2-methoxycarbonylaminoallylphenoxy)propanol-2.
(12) 1-[2-(4-morpholinylcarbonylphenoxy)ethylamino]-3-(2-allylphenoxy)propanol-2.
(13) 1-[1-methyl-2-(4-carbamylphenoxy)ethylamino]-3-(2-methylisonitrisomethylphenoxy)propanol-2.
(14) 1-[4-(2-(2-methoxycarbonylamino)ethyl)phenoxyethylamino]-3-(2-methylphenoxy)-propanol-2.
(15) 1-[2-(4-carbamylphenoxy)ethylamino]-3-(3-allylphenoxy)propanol-2.
(16) 1-[2-(4-carbamylphenoxy)ethylamino]-3-(2-chlorophenoxy)propanol-2.
(17) 1-[2-(4-carbamylphenoxy)ethylamino]-3-(2,3-dichlorophenoxy)propanol-2.
(18) 1-[2-(4-carbamylphenoxy)ethylamino]-3-[2-(ω-hydroxyethylaminocarbonylmethoxy)phenoxy]-propanol-2.
(19) 1-[2-(4-carbamylphenoxy)ethylamino]-3-[2-(ω-hydroxyethylaminocarbonylmethoxy)phenoxy]-propanol-2.

As is apparent from the foregoing disclosure of preferred embodiments of the present invention, as well as from the following examples, some particular groups of compounds have been specifically considered within the scope of the foregoing invention. These specific groups of compounds suitable for use as adrenergic β receptor blocking agents are the following:

GROUP I. COMPOUNDS OF THE FORMULA

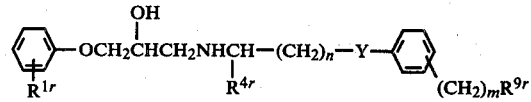

wherein $R^{1r}$ is in the 2- or 3-position and selected from the group consisting of —$CH_2CH=CH_2$, —$OCH_2CH=CH_2$, —$OCH_2\equiv CH$, alkoxycarbonylaminoalkoxy, alkoxyalkoxy and —C=NOR, wherein R is hydrogen or alkyl having 1 to 3 carbon atoms;

$R^{4r}$ is selected from the group consisting of hydrogen and alkyl;

$R^{9r}$ is selected from the group consisting of hydrogen, alkoxycarbonylamino, $CONH_2$, and morpholino;

Y is a divalent member selected from the group consisting of O and $CH_2$;

n is an integer from 0 to 5 exclusive;

m is an integer from 0 to 2 exclusive;

when $R^{9r}$ is hydrogen, m being at least 1.

GROUP II. COMPOUNDS OF THE FORMULA

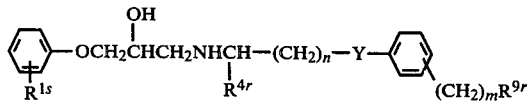

wherein $R^{1s}$ is selected from the group consisting of ethyl, N-propyl, isopropyl, N-butyl, secondary butyl or tertiary butyl;

$R^{4r}$ is selected from the group consisting of hydrogen, alkoxycarbonylamino, $CONH_2$, and morpholino;

Y is a divalent member selected from the group consisting of O and $CH_2$;

n is an integer from 0 to 5 exclusive;

m is an integer from 0 to 2 exclusive;

when $R^{9r}$ is hydrogen, m being at least 1.

GROUP III. COMPOUNDS OF THE FORMULA

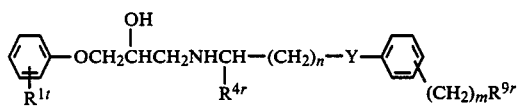

wherein $R^{1t}$ is selected from the group consisting of $OCH_2CONHCH_2CH_2OH$ and $OCH_2CONHCH_2CH_2OCH_3$;

$R^{4r}$ is selected from the group consisting of hydrogen and alkyl;

$R^{9r}$ is selected from the group consisting of hydrogen, alkoxycarbonylamino, $CONH_2$, and morpholino;

Y is a divalent member selected from the group consisting of O and $CH_2$;

n is an integer from 0 to 5 exclusive;

m is an integer from 0 to 2 exclusive;

when $R^{9r}$ is hydrogen, m being at least 1.

GROUP IV. THE COMPOUND OF THE FORMULA

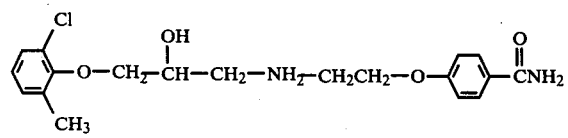

The most interesting compounds of the present invention are those in which $R^{1r}$ is 2—CH≡CCH$_2$O— or 2—CH$_2$≡CHCH$_2$O—, $R^{6r}$ is H, $R^{9r}$ is 4—H$_2$NCO—, Y is —O—, n is 1 and m is 0. A second group of important compounds are those in which $R^{1r}$ is 2—CH≡CCH$_2$O—, or 2—CH$_2$≡CHCH$_2$O—, $R^{6r}$ is methyl, $R^{9r}$ is 4—H$_2$NCO—, Y is —O—, n is 1 and m is 0. Another important group are those in which $R^1$ is 2—RON—CH— or 2-alkyl. Also important are compounds in which $R^1$ is alkoxy or alkoxycarbonylamino alkoxy. $R^{9r}$ is preferably carbonyl in all cases.

The new compounds are obtained in accordance to methods known per se. Thus, a compound of formula II

wherein Ar, $R^1$, $R^2$ and $R^3$ have the meanings given above, $X^1$ is a hydroxy group and Z is a reactive, esterified hydroxy group, or $X^1$ and Z together form an epoxy group, is reacted with an amine of the formula (III)

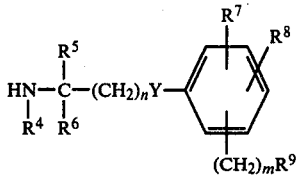

wherein $R^4$, $R^5$, $R^6$, $R^7$, $R^8$, $R^9$, Y, m and n have the same meanings as given above.

A reactive, esterified hydroxy group is particularly a hydroxy group esterified with a strong, inorganic or organic acid, preferably a hydrohalogen acid, such as hydrochloric acid, hydrobromic acid, or hydroiodic acid, further sulphuric acid or a strong organic sulphonic acid such as a strong aromatic sulphonic acid, e.g. benzenesulphonic acid, 4-bromobenzenesulphonic acid or 4-toluenesulphonic acid. Thus, Z is preferably chloro, bromo or iodo.

This reaction is carried out in a common way. When using a reactive ester as a starting material the preparation takes place preferably in the presence of a basic condensing agent and/or with an excess of an amine. Suitable basic condensing agents are e.g. alkali metal hydroxides such as sodium or potassium hydroxide, alkali metal carbonates such as potassium carbonate and alkali metal alcoholates such as sodium methylate, potassium ethylate and potassium tert.butylate.

Further, a compound of formula IV

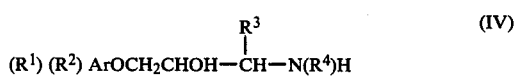

wherein Ar, $R^1$, $R^2$, $R^3$ and $R^4$ have the same meanings as given above, is reacted with a compound of the formula V

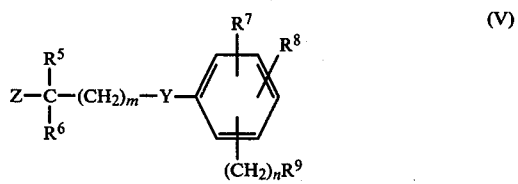

wherein $R^5$, $R^6$, $R^7$, $R^8$, $R^9$, Y, m, n and Z have the same meanings as given above.

This reaction is carried out in a common way, preferably in the presence of a basic condensing agent and/or an excess of an amine. Suitable basic condensing agents are e.g. alkaline alcoholates, preferably sodium or potassium alcoholate, or also alkaline carbonates such as sodium or potassium carbonate.

Further, a compound of formula VI

wherein Ar, $R^1$ and $R^2$ have the same meanings as given above and M is hydrogen or an alkali metal is reacted with a compound of formula VII

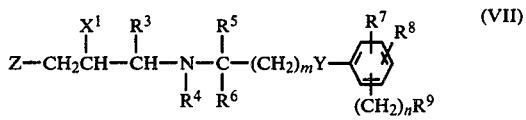  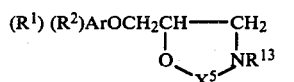 (VII) (VIII)

wherein $R^3$, $R^4$, $R^5$, $R^6$, $R^7$, $R^8$, $R^9$, m, n, Y, Z and $X^1$ have the same meanings as given above.

This reaction is carried out in a common way. In those cases where reactive esters are used as starting material, the compound of formula VI may suitably be used in the form of its metal phenolate such as alkali phenolate, preferably sodium phenolate, or one works in the presence of an acid binding agent, preferably a condensing agent, which can form a salt of the compound of formula VI as an alkali metal alcoholate.

Further, one may split off a residue from a compound of formula I above, wherein $R^1$, $R^2$, $R^3$, $R^4$, $R^5$, $R^6$, $R^7$, $R^8$, $R^9$, Y, m, and n have the same meanings as above and in which the nitrogen atom of the amino group and/or the hydroxy group has attached thereto a splitable residue.

Such splitable residues are especially those which are splitable by solvolysis, reduction, pyrolysis or fermentation.

Residues splitable by solvolysis are preferably residues splitable by hydrolysis or ammonolysis.

Residues splitable by means of hydrolysis are e.g. an acyl residue, which, when present, are functionally varied carboxy groups, e.g. oxycarbonyl residues, as alkoxycarbonyl residues, e.g. tert. butoxycarbonyl residue, or ethoxycarbonyl residue, aralkoxycarbonyl residues such as phenylloweralkoxycarbonyl residues, e.g. a carbobenzyloxy residue halogencarbonyl residue, e.g. a chlorocarbonyl residue, further arylsulphonyl residues such as toluene sulphonyl or bromobenzenesulphonyl residues and possibly as halogenated, as fluorinate loweralkanoyl residues such as the formyl-, acetyl-, or trifluoroacetyl residue or a benzyl residue or cyano groups or silyl residues, such as a trimethylsilyl residue.

Of the above mentioned residues present at the hydroxy groups, which residues are splitable by hydrolysis preferably, the oxycarbonyl residues and the loweralkanoyl residues or the benzoyl residues are used.

Besides the above mentioned also double-bounded residues, which are splitable at the amino group by hydrolysis are used, e.g. alkylidene residue or a phosphorylidene group such as a triphenylphosphorylidene group, whereby the nitrogen atom then obtains a positive charge.

Residues splitable at the hydroxy group and the amino group by hydrolysis are furthermore divalent residues such as in occurring cases substituted methylene. As substituents on the methylene residues any organic residue may be used, whereby it does not matter at the hydrolysis which compound is the substituent to the methylene residue. As methylene substituents e.g. aliphatic or aromatic residues such as alkyl as mentioned above, aryl, e.g. phenyl or pyridyl may be used. The hydrolysis may be carried out in any common way, suitably in a basic or preferably in an acid medium.

Compounds having residues which are splitable by hydrolysis are also the compounds according to formula VIII, when $R^4$ is hydrogen wherein Ar, $R^1$ and $R^2$ have the same meanings as given above, $R^{13}$ is the group of the formula IX

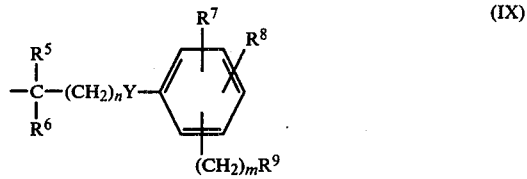

and $X^5$ is a carbonyl or thiocarbonyl residue.

The hydrolysis is carried out in an analogous way, e.g. in the presence of a hydrolyzing agent, e.g. in the presence of acidic agent such as e.g. diluted mineral acids, as sulphoric acid or hydrohalogen acid, or in the presence of basic agents such as e.g. alkali metal hydroxides such as sodium hydroxide. Oxycarbonyl residues, aryl sulphonyl residues and cyano groups may in a suitable way be split off by means of acidic agents as by means of a hydrohalogen acid, suitably hydrobromic acid. Preferably the splitting may take place using diluted hydrobromic acid, possibly in a mixture with acetic acid. Cyano groups are preferably split off by means of hydrobromic acid at an elevated temperature, as in boiling hydrobromic acid, according to the "bromocyano method" (v. Braun). Further, e.g. a tert.-butoxy-carbonyl residue may be split off under anhydrous conditions by means of a treatment with a suitable acid, such as trifluoroacetic acid. Acidic agents are preferably used in hydrolysis of compounds of formula VI.

Residues splitable by ammonolysis are especially the halogencarbonyl residues, such as the chlorocarbonyl residue. The ammonolysis may be carried out in a common way, e.g. by means of an amine containing at least one hydrogen atom bounded to the nitrogen atom, as a mono- or diloweralkylamine, e.g. methylamine or dimethylamine, or especially ammonia, preferably at an elevated temperature. Instead of ammonia one may use an agent which gives ammonia such as hexamethylenetetraamine.

Residues splitable by means of a reduction are e.g. an α-aralkoxycarbonyl residue such as a benzyloxycarbonyl residue, which in a common way may be split off by a hydrogenolysis, especially by catalytically activated hydrogen, as by hydrogen in the presence of hydrogenating catalysts, e.g. Raney-nickel. Further residues splitable by means of hydrogenolysis are 2-halogenalkoxycarbonyl residues such as 2,2,2-trichloroethoxycarbonyl residues or 2-iodoethoxy- or 2,2,2-tribromoethoxycarbonyl residues, which may be split off in a common way, suitably by means of a metallic reduction (so called nascent hydrogen). Nascent hydrogen may be obtained by the influence of metal or metal alloys, such as amalgam on compounds which give hydrogen such as carboxy acids, alcohols or water, whereby especially zinc or zinc alloys together with acetic acid may be used. Hydrogenolysis of 2-halogenalkoxycarbonyl residues may further take place using chromium or chromium (II) compounds such as chromium (II) chloride or chromium (II) acetate.

A residue splitable by reduction may also be an arylsulphonyl group such as a toluenesulphonyl group, which in a common way may be split off by reduction using nascent hydrogen, e.g. by means of an alkali metal, such as lithium or sodium in liquid ammonia, and suitably may be split off from a nitrogen atom. In carrying out the reduction one has to take care that other reducing groups are not influenced.

Residues splitable by means of pyrolysis, especially residues splitable from the nitrogen atom, are in ocurring cases substituted suitably unsubstituted carbamoyl groups. Suitable substituents are e.g. loweralkyl or arylloweralkyl such as methyl or benzyl or aryl, as phenyl. The pyrolysis is carried out in a common way, whereby one may have to take care of other thermically susceptible groups.

Residues splitable by means of fermentation, especially residue splitable from the nitrogen atom are in occurring cases substituted, however suitably unsubstituted carbamoyl groups. Suitable substituents are e.g. loweralkyl or arylloweralkyl, such as methyl or benzyl, or aryl such as phenyl. The fermentation is carried out in a common way, e.g. by means of the enzyme urease or soy bean extract at about 20° C. or a slightly elevated temperature.

Further, a Schiff's base of formula X or XI when $R^4$, $R^5$ and $R^6$ are hydrogen,

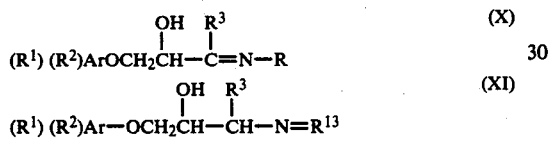

or a cyclic tautomer corresponding to formula XI of formula XII

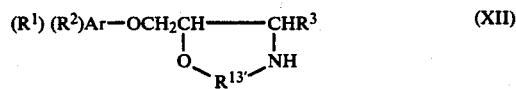

can be reduced, wherein Ar, $R^1$, $R^2$, $R^3$, and $R^{13}$ have the same meanings as given above and $R^{13'}$ is the same as $R^{13}$ and whereby the compounds of formula XI and XII exist together, too. This reduction is carried out in a common way, e.g. using a di-lightmetal hydride, such as sodium boronhydride, lithium aluminium hydride, using a hydride such as Boran with formic acid, or by means of a catalytic hydrogenation, as with hydrogen in the presence of Raney nickel. In the reduction one has to take care that other groups are not affected.

Further, the oxo group in the compound of formula XIII

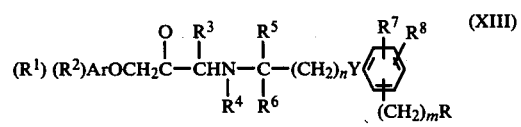

wherein Ar, $R^1$, $R^2$, $R^3$, $R^4$, $R^5$, $R^6$, $R^7$, $R^8$, $R^9$, m, n and Y have the same meanings as given above, can be reduced to a hydroxy group. This reduction is carried out in a common way, especially using a di-lightmetal hydride, as mentioned above, or according to the "Meerwein-Pondorf-Verley" method, or a modification thereof, suitably using an alkanol as a reaction component and as a solvent, as isopropanol, and using a metal alkanolate such as metal isopropanolate, e.g. aluminium isopropanolate.

Further, in a compound of formula XIV

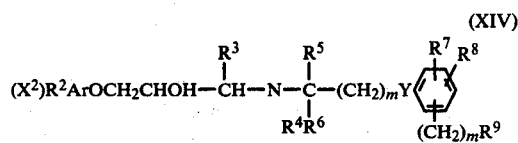

wherein Ar, $R^2$, $R^3$, $R^4$, $R^5$, $R^6$, $R^7$, $R^8$, $R^9$, m, n, and Y have the same meanings as given above, and wherein $X^2$ is a residue which is able to be transformed in to a residue $R^1$ having the same meaning as given above, one transforms $X^2$ to $R^1$.

A residue $X^2$ able to be transformed into $R^1$ is e.g. a residue $X^2$ transformable to a alkoxyalkyl residue $R^1$, as a $Z^1$-alkyl residue. A compound XIV having such a residue $Z^1$ alkyl as $X^2$ can be reacted in a common way with a compound alkyl-$Z^2$, whereby one of $Z^1$ and $Z^2$ is a hydroxy group and the other being Z having the meaning given above. Thus, one can react either a compound of formula XV

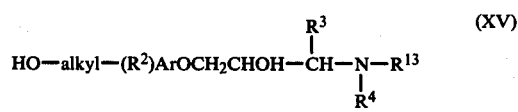

with a compound alkyl-Z, or a compound of formula XVI

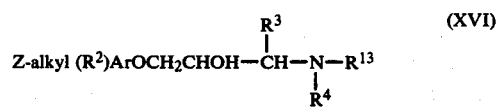

with a compound alkyl—OH, whereby $R^2$, $R^3$, $R^4$, $R^{13}$ and Z have the same meanings as given above. The reaction is carried out in a common way e.g. as the reaction of a compound of formula II with an amine

A residue $X^2$ transformable into $R^1$ is e.g. a residue $X^2$, transformable into a alkoxyalkoxy residue $R^1$ as a residue $Z^1$-alkyl—O— or a hydroxy group.

A compound XIV having such a residue $Z^1$-alkyl—O— as $X^2$ can be reacted in a common way with a compound alkyl-$Z^2$, whereby one of the residues $Z^1$ and $Z^2$ is hydroxy and the other being Z having the same meaning as given above.

Thus, one can react a compound of formula XVII

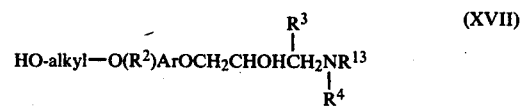

with a compound alkyl-Z or a compound of formula XVIII

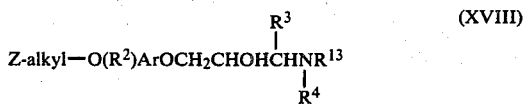

with a compound alkyl-OH, whereby $R^2$, $R^3$, $R^4$, $R^{13}$ and Z have the same meanings as given above. The reaction is carried out in a common way, e.g. as the reaction of a compound of formula II with an amine

A compound of formula XIV having a hydroxy group as a residue $X^2$ can be reacted in a common way with a compound alkoxyalkyl-Z, whereby Z has the same meaning as above.

Thus, one can react a compound of formula XIX

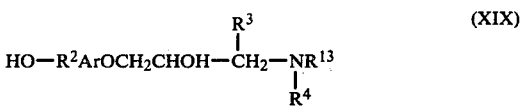

with a compound alkoxyalkyl-Z, wherein $R^2$, $R^3$, $R^4$, $R^{13}$ and Z have the same meanings as given above. The reaction is carried out in a common way, e.g. as the reaction of a compound of formula II with an amine

Further, the oxo group in a compound corresponding to these of formula I i.e. in the cases when $R^3$, $R^5$ and $R^6$ are hydrogen and which carries an oxo group at a carbon atom bound to a nitrogen atom may be reduced to two hydrogen atoms. The residue $R^1$ is thereby preferably not one of the residues containing a carbonyl group

Said compound are e.g. such of the formula XX

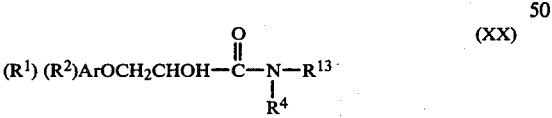

wherein $R^1$, $R^2$, $R^4$ and $R^{13}$ have the meaning given above, when $R^3$ is hydrogen.

The reduction can be carried out according to the above described manner using complexed methylhydrides, e.g. lithium aluminium hydride or diisobutylaluminium hydride. Suitably the reaction takes place in an inert solvent such as ether, e.g. diethylether or tetrahydrofuran.

In a common way the substituents may be varied from the compounds obtained within the end product, and also the compounds obtained may be introduced; split off or transformed into other end products in a common way.

Thus, it is possible to hydrogengate catalytically C-C double bonds or C-C triple bonds to C-C single bonds by means of hydrogen in the presence of a hydrogenation catalyst, e.g. platinum, palladium or nickel, such as Raney-nickel. Thereby one has to take care that other reducible groups are not reduced.

In compounds obtained containing a C-C triple bond this may further be transformed into a C-C double bond and, if desired, be hydrogenated stereospecifically into C-C-cis or C-C trans double bond. The hydrogenation of C-C triple bond to a C-C double bond may for example be carried out using 1 mole of hydrogen in the presence of a less active hydrogenation catalyst such as iron or palladium, e.g. Raney-iron or palladium with barium sulphate, preferably at an elevated temperature. The hydrogenation to a C-C-cis double bond may take place e.g. between 1 mole of hydrogen and a desactivated catalyst, such as palladium on active carbon and in the presence of quinoline, palladium on calcium carbonate in the presence of plumbum salts or Raney-nickel.

The hydrogenation to a C-C-trans double bond may take place by means of sodium in liquid ammonia, whereby with regard to other reducible groups short reaction times are used and no excess of the reducing agent is used, possibly an ammonium halide, such a ammonium chloride, being added as a catalyst.

In the reduction mentioned above, one has to see to that no further reducible groups are reduced. In the reduction using Raney-nickel and hydrogen one has to consider especially a possibly present halogen atom bond to the aromatic ring, so that it is not replaced by hydrogen. Furthermore, in all reductions, especially catalytic hydrogenations, one has to consider any thioether group present. Preferably sulphur-resistant catalysts are used and, in the actual cases, the volume of hydrogen to be absorbed is calculated and when the calculated amount is absorbed in the hydrogenation, reduction is finished.

A residue $X^2$ transformable into $R^1$ is e.g. a residue $X^2$ transformable into an alkoxycarbonylaminoalkoxy residue $R^1$, e.g. a hydroxy group.

A compound XIV with a hydroxy group as $X^2$ can be reacted in a common way with an alkoxycarbonylaminoalkyl-Z residue.

Thus, one can react a compound of formula XIX

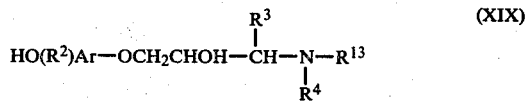

with an alkoxycarbonylamino-Z whereby $R^2$, $R^3$, $R^4$, $R^{13}$ and Z have the meanings given above. The reaction is carried out in a common way, e.g. as it has been mentioned for the reaction of a compound of formula III with an amine

A residue $X^2$ transformable into $R^1$ is e.g. a residue $X^2$ transformable into an alkoxycarbonylaminoalkoxy residue $R^1$, such as a residue $H_2N$-alkoxy.

A compound XIV having such a residue $H_2N$-alkoxy can in a common way be reacted with an alkoxycarbonylchloride.

Thus one can react a compound of the formula XXI

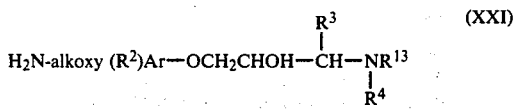

with an alkoxycarbonylchloride, whereby $R^2$, $R^3$, $R^4$, and $R^{13}$ have the meanings given above. The reaction is carried out in a common way, e.g. as it has been mentioned for the reaction of a compound of formula III with an amine

A residue transformable into $R^1$ is e.g. a residue $X^2$ transformable into a residue alkoxycarbonylaminoalkoxy $R^1$, such as a residue $Z^1$—CO—NH-alkoxy.

A compound XIV having such a residue $Z^1$—CO—NH-alkoxy as $X^2$ can in a common way be reacted with a compound alkyl-$Z^2$, wherein $Z^1$ and $Z^2$ have the meanings given above.

Thus, one can react a compound of the formula XXII

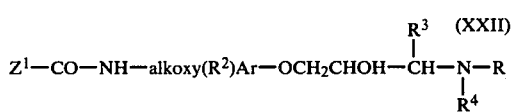

with a compound alkyl-$Z^2$, wherein $R^2$, $R^3$, $R^4$, $R^{13}$, $Z^1$ and $Z^2$ have the meanings given above.

A residue $X^2$ transformable into $R^1$ is e.g. a residue $X^2$ transformable into alkoxycarbonylaminoalkyl residue $R^1$, such as a residue $H_2N$-alkyl.

A compound XIV having such a residue $H_2N$-alkyl can in a common way be reacted with an alkoxycarbonylchloride.

Thus, one can react a compound of the formula XXIII

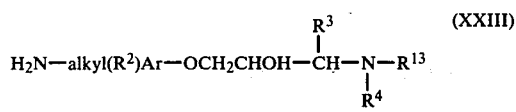

with an alkoxycarbonylchloride, wherein Ar, $R^2$, $R^3$, $R^4$ and $R^{13}$ have the meanings given above. The reaction is carried out in a common way e.g. as has been mentioned for the reaction of a compound of formula III with an amine.

A residue transformable into $R^1$ is e.g. a residue $X^2$ transformable into a residue alkoxycarbonylaminoalkyl $R^1$, such as a residue $Z^1$—CO—NH—loweralkyl.

A compound XI having such a residue $Z^1$—CO—N-H—alkyl as $X^2$ can in a common way be reacted with a compound alkyl-$Z^2$, wherein $Z^1$ and $Z^2$ have the meanings given above.

Thus, one can react a compound of the formula XXII

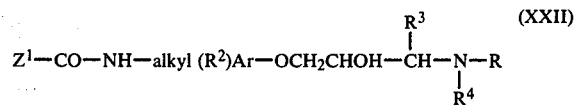

with a compound alkyl-$Z^2$, wherein Ar, $R^2$, $R^3$, $R^4$, $R^{13}$, $Z^1$ and $Z^2$ have the meanings given above.

A residue $X^2$ transformable into $R^1$ is e.g. a residue $X^2$ transformable into an alkoxycarbonylaminoalkenyl residue $R^1$, such as a residue Z-alkenyl.

A residue $X^2$ transformable into $R^1$ is e.g. a residue $X^2$ transformable into an alkoxycarbonylaminoalkenyl residue $R^1$, such as a residue $H_2N$-alkenyl.

A compound XIV having such a residue $H_2N$-alkenyl can in a common way be reacted with an alkoxycarbonylchloride.

Thus, one can react a compound of the formula XXIV

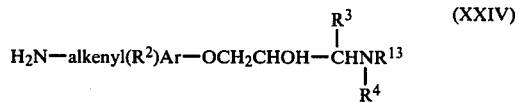

with an alkoxycarbonylchloride, wherein $R^2$, $R^3$, $R^4$ and $R^{13}$ have the meanings given above. The reaction is carried out in a common way e.g. as has been mentioned for the reaction of a compound of formula III with an amine

A residue transformable into $R^1$ is e.g. a residue $X^2$ transformable into a residue alkoxycarbonylaminoalkenyl $R^1$, such as a residue $Z^1$—CO—NH-alkenyl.

A compound XI having such a residue $Z^1$—CO—NH-alkenyl as $X^2$ can in a common way be reacted with a compound alkyl-$Z^2$, wherein $Z^1$ and $Z^2$ have the meanings given above.

Thus, one can react a compound of the formula XXI

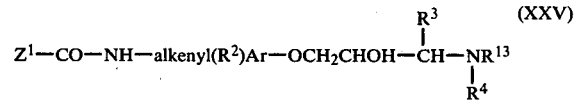

with a compound alkyl-$Z^2$, wherein $R^2$, $R^3$, $R^4$, $R^{13}$, $Z^1$ and $Z^2$ have the meanings given above.

Further in a compound of formula XXVI

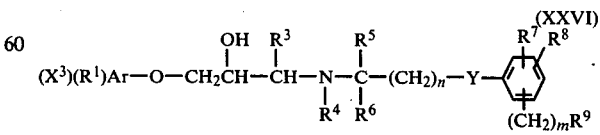

one transforms $X^3$ to $R^2$ wherein Ar, $R^1$, $R^3$, $R^4$, $R^5$, $R^6$, $R^7$, $R^8$, $R^9$, m, n, and Y have the meanings given above and $X^3$ is a residue which is able to be transformed to a residue $R^2$ having the same meaning as given above.

A compound of formula XXVI having a hydroxy group as a residue $X^3$ can be reacted in a common way with a compound alkyl-Z wherein Z has the same meaning as above.

Thus, one can react a compound of formula XXVII

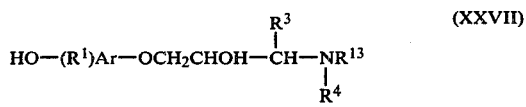

with a compound alkyl-Z, wherein Ar, $R^1$, $R^3$, $R^4$, $R^{13}$ and Z have the meanings given above. The reaction is carried out in a common way, e.g. as the reaction of a compound of formula II with an amine of formula III.

Further in a compound of formula XXVIII

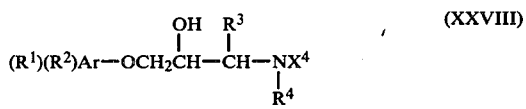

one transforms $X^4$ to $R^{13}$, wherein Ar, $R^1$, $R^2$, $R^3$ and $R^4$ have the same meanings as given above and wherein $X^4$ is a residue which is able to be transformed to a residue $R^{13}$ having the same meaning as given above.

A residue $X^4$ able to be transformed into $R^{13}$ is e.g. a residue $X^4$ transformable to a (substituted)-phenoxyalkyl, residue $R^{13}$, such as a $Z^3$-alkyl residue. A compound XXXII having such a residue $Z^3$-alkyl as $X^4$ can be reacted in a common way with a compound (substituted)phenyl-$Z^4$, whereby one of $Z^3$ and $Z^4$ is a hydroxy group and the other being Z having the meaning given above. Thus, one can react either a compound of formula XXIX

with a compound (substituted)-phenyl-Z, or a compound of formula XXX

with a compound (substituted)-phenyl-OH, whereby $R^5$, $R^6$ and n have the same meanings as given above, and $R^{14}$ is

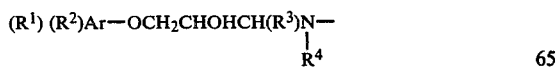

wherein Ar, $R^1$, $R^2$, $R^3$ and $R^4$ have the same meanings as given above. The reaction is carried out in a common way e.g. as the reaction of a compound of formula II with an amine of formula III

Further in a compound of the formula XXXI

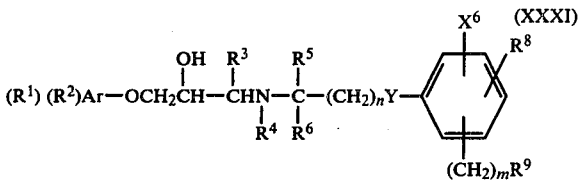

wherein Ar, $R^1$, $R^2$, $R^3$, $R^4$, $R^5$, $R^6$, $R^8$, $R^9$Y, n, and m have the meanings as above, and $X^6$ is a residue transformable to $R^7$ having the above meaning, $X^6$ is transformed to $R^7$.

A residue $X^6$ able to be transformed into $R^7$ is e.g. a residue $X^6$ transformable into an alkoxy residue $R^7$, such as a residue

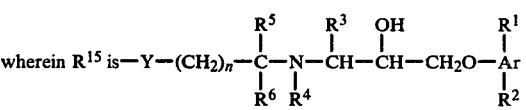

A compound having such a residue as $X^6$ can be reacted in a common way with a compound alkyl-$Z^2$, $Z^1$ and $Z^2$ having the meanings as above. Thus, one can react either a compound of formula XXXII

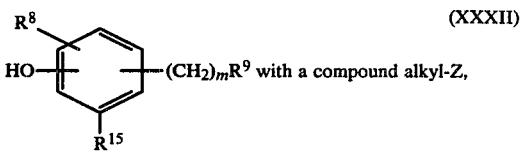

or a compound of formula XXXIII

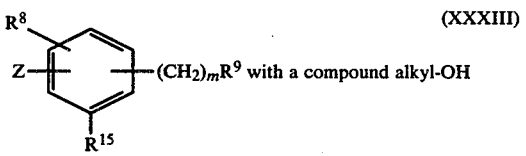

whereby $R^{15}$, $R^8$, $R^9$ and m have the above meanings.

Further in a compound of the formula XXXIV

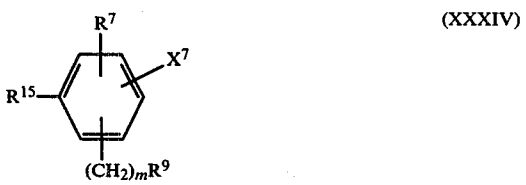

wherein $R^{15}$, $R^7$, $R^9$ and m have the above meanings, and $X^7$ is a residue transformable to $R^8$ having the above meaning, $X^7$ is transformed to $R^8$.

A residue $X^7$ able to be transformed into $R^7$ is e.g. a residue $X^7$ transformable into an alkoxy residue $R^8$, such as a residue

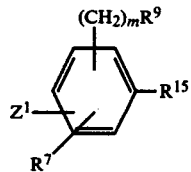

A compound having such a residue as $X^7$ can be reacted in a common way with a compound alkyl-$Z^2$, $Z^1$ and $Z^2$ having the above meanings. Thus one can react either a compound of formula XXXV

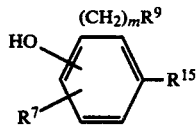 (XXXV)

with a compound alkyl-Z, or a compound of formula XXXVI

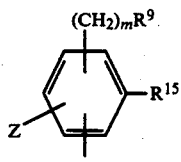 (XXXVI)

with a compound alkyl—OH wherein $R^{15}$, $R^7$, $R^9$, m and Z have the above meanings.

Further in a compound of the formula XXXVI

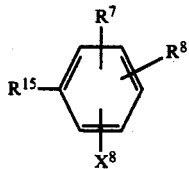 (XXXVII)

$X^8$ is transformed to —$(CH_2)_mR^9$, wherein $R^{15}$, $R^7$ and $R^8$ have the above meaning, and $X^8$ is a residue transformable to —$(CH_2)_mR^9$, m and $R^9$ having the above meanings.

A residue $X^8$ able to be transformed into —$(CH_2)_mR^9$ is e.g. a residue $X^8$ transformable into a —$(CH_2)_m$CONR$^{10}$R$^{11}$, and a —$(CH_2)_m$CONHNR$^{10}$R$^{11}$, when $R^{10}$ and $R^{11}$ together with adjacent nitrogen form a morpholinyl or piperazinyl group, such as a residue

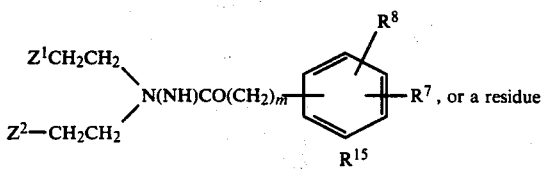

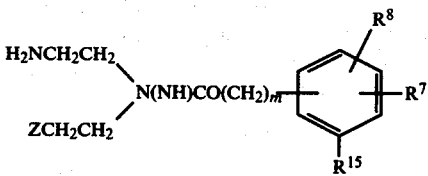

wherein $R^7$, $R^8$, $R^9$, $R^{15}$, m, Z, $Z^1$ and $Z^2$ have the above meanings. These residues are each reacted to ring closure in a common way, e.g. as the reaction between a compound of formula II with a compound of formula III.

A residue $X^8$ able to be transformed into —$(CH_2)_mR^9$ is e.g. a residue $X^8$ transformable into a —$(CH_2)_m$CONR$^{10}$R$^{11}$, or a —$(CH_2)_m$CONHNR$^{10}$R$^{11}$, such as a residue

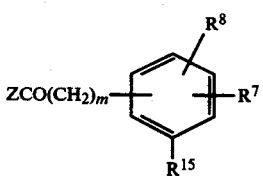

which is reacted in a common way with a compound $R^{10}R^{11}$N—H or a compound $R^{10}R^{11}$NNH$_2$.

The reaction is carried out in the same way as the reaction between a compound of formula II and a compound of formula III.

A residue $X^8$ able to be transformed into $(CH_2)_mR^9$ is e.g. residues $X^8$ transformable into an alkoxycarbonylaminoalkyl—$(CH_2)_m$ residue —$(CH_2)_mR^9$. These reactions and residues are the same as for the cases when $X^2$ is a residue transformable into an alkoxycarbonylaminoalkyl residue $R^1$.

Further in a compound of the formula XL

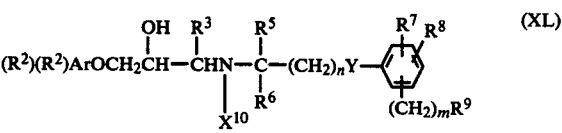 (XL)

wherein Ar, $R^1$, $R^2$, $R^3$, $R^5$, $R^6$, $R^7$, $R^8$, $R^9$, Y, m and n have the above meanings, and $X^{10}$ is a residue transformable to $R^4$ being hydrogen $X^{10}$ is transformed into $R^4$.

A residue $X^{10}$ able to be transformed into $R^4$ being hydrogen is $X^{10}$ being benzyl or alkanoyl which is hydrolyzed.

The above mentioned reactions may possibly be carried out simultaneously or after each other in any sequence.

The above mentioned reactions are carried out in a manner known per se in the presence or absence of diluting, condensing and/or catalytical agents at a low room or an elevated temperature, possibly being carried out in a closed vessel.

Depending on the process conditions and the starting material, the end product is obtained either in free form or in the form of its acid addition salt, which is included in the scope of the invention.

Thus, for example, basic, neutral or mixed salts may be obtained as well as hemiamino, sesqui-or polyhydrates. the acid addition salts of the new compounds may in a manner known per se be transformed into free compounds using e.g. basic agents such as alkali or ion exchanger. On the other hand, the free bases obtained may form salts with organic or inorganic acids. In the preparation of acid addition salts preferably such acids are used which form suitable therapeutically acceptable salts. Such acids are e.g. hydrohalogen acids, sulphuric acid, phosphoric acid, nitric acid, perchloric acid, aliphatic, alicyclic aromatic or heterocyclic carboxy or sulphonic acids, such as formic acetic, propionic, succinic, glycolic, latic, malic, tartaric, citric, ascorbic, maleic, hydroxymaleic or pyruvic acid, phenylacetic, benzoic, p-aminobenzoic, anthranilic, p-hydroxybenzoic, salicyclic or p-aminosalicyclic acid, embonic acid, methanesulphonic, ethanesulphonic, hydroxyethanesulphonic, ethylenesulphonic acids, halogenbenzenesulphonic, toluenesulphonic, naphthylsulphonic acids or sulphanilic acid, methionine, tryptophane, lysine or arginine.

These or other salts of the new compounds such as e.g. picrates may serve as purifying agents of the free bases obtained as the free bases are transformed into salts, these are separated and the bases are then set free from the salts again. According to the close relationship between the new compounds in free form and in the form of their salts it will be understood from the above and the below that, if possible, the corresponding salts are included when the free compound is mentioned.

The invention also relates to any embodiment of the process of which one starts from any compound obtained as an intermediate in any process step and one carries out the lacking process step, or one breaks off the process at any step, or at which one forms a starting material under the reaction conditions, or at which a reaction component possibly in the form of its salt is present.

Thus, one may react an aldehyde of the formula XXXVIII

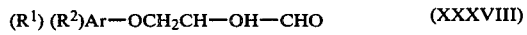

$(R^1) (R^2)Ar—OCH_2CH—OH—CHO$ (XXXVIII)

wherein $R^1$ and $R^2$ have the same meaning as given above, with an amine of the formula

HN—$R^{13}$
|
$R^4$ wherein $R^4$ and $R^{13}$ have the same meanings as given above, in the presence of a suitable reducing agent, such as one of the above mentioned. Thereby a compound of formula X is obtained as an intermediate, which then is reduced according to the invention.

Further, one may in a manner known per se react an amine of the formula III with an aldehyde or a ketone of the formula O=$R^{13'}$, wherein $R^{13'}$ has the above meaning, in the presence of a suitable reducing agent, such as one of the above mentioned. Thereby a compound of formula XI or XII is obtained as a intermediate, which then is reduced according to the invention.

Further, one may in a manner known per se react a phenol of formula V above with an acetidinol of the formula XXXIX

$$\begin{array}{c} CH_2 —— N—R^{13} \\ | \quad\quad\quad | \\ HO—CH————CH_2 \end{array}$$ (XXXIX)

wherein $R^{13}$ has the meaning given above, to a compound of formula I.

This reaction is carried out in a common way. Thus the reaction is carried out under alkaline conditions in a suitable solvent, such as benzylalcohol by boiling the reaction mixture for some hours. Thereby the phenol is primarily converted to its metalphenolate such as alkalimetalphenolate before it is added to the acetidinol of formula XXX.

It is obvious from the above described methods for preparing the compounds of the invention that that different substituents can be added by analogous processes. Thus the addition of $—OCH_2CH=CH_2$ and $—OCH_2C\equiv CH$ groups as $R^1$ can be done in the same way as the addition of alkoxy groups as $R^2$. Analogous, alkoxy groups $R^7$ and $R^8$ can be added in the same way as alkoxy $R^2$. Similar analogs can be done for other radicals.

The new compounds may, depending on the choice of starting material and process, be present as optical antipodes or racemate, or, if they contain at least one asymmetric carbon atom, be present as an isomer mixture (racemate mixture).

The isomer mixtures (racemate mixtures) obtained may, depending on physical-chemical differences of the components, be separated into both the stereoisomeric (diastereomeric) forms e.g. by means of chromatography and/or fractionated cyrstallization.

The racemates obtained can be separated according to known methods, e.g. by means of recrystallization from an optically active solvent, by means of microorganisms, or by a reaction with optically active acids forming salts of the compound and separating the salts thus obtained, e.g. by means of their different solubility in the diastereomeres, from which the antipodes by the influence of a suitable agent may be set free. Suitably useable optically active acid are e.g. the L- and D-forms of tartaric acid, di-o-tolyltartaric acid, malic acid, mandelic acid, camphersulfonic acid or china acid. Preferably the more active part of two antipodes is isolated.

Suitably such starting materials are used for carrying out the reactions of the invention, which material leads to groups of end products primarily especially to the specifically described and preferred end products.

The starting materials are known or may, if they should be new, be obtained according to processes known per se.

In clinical use the compounds of the invention are administered normally orally, rectally or by injection in the form of a pharmaceutical preparation, which contains an active component either as free base or as pharmaceutically acceptable non-toxic acid addition salt, as e.g. the hydrochloride, lactate, acetate, sulphamate or the like in combination with a pharmaceutically acceptable carrier. Where the new compounds of the invention are mentioned reference is made to either the free amine base or the acid addition salts of the free base, even if the compounds are generally or specifically described, provided that the context in which such expressions are used permits such latitude. The carrier may be a solid, semi-solid or liquid diluent or a capsule. These pharmaceutical preparations are a further object of the invention. Usually the amount of active compound is between 0.1 to 95% by weight of the preparation, suitably between 0.5 to 20% by weight in preparations for injection and between 2 to 50% by weight in preparations for oral administration.

In the preparation of pharmaceutical preparations containing a compound of the present invention in the form of dosage units for oral administration the compound selected may be mixed with a solid, pulverulent carrier, such as e.g. with lactose, saccharose, sorbitol, mannitol, starch, such as potato starch, corn starch, amylopectin, cellulose derivatives or gelatine, as well as with an antifriction agent such as magnesium stearate, calcium stearate, polyethyleneglycol waxes or the like, and be pressed into tablets. If coated tablets are wanted, the above prepared core may be coated with concentrated solution of sugar, which solution may contain e.g. gum arabicum, gelatine, talc titaniumdioxide or the like. Furthermore, the tablets may be coated with a lacquer dissolved in an easily volatile organic solvent or mixture of solvents. To this coating a dye may be added in order easily to distinguish between tablets with different active compounds or with different amounts of the active compound present.

In the preparation of soft gelatine capsules (pear-shaped, closed capsules), which consist of gelatine and e.g. glycerine or in the preparation of similar closed capsules the active compound is mixed with a vegetable oil. Hard gelatine capsules may contain granules of the active compound in combination with a solid, pulverulent carrier such as lactose, saccharose, sorbitol, mannitol, starch, (e.g. potato starch, corn starch or amylopectin), cellulose derivatives or gelatine.

Dosage units for rectal administration may be prepared in the form of suppositories, which contain the active substance in a mixture with a neutral fat base, or they may be prepared in the form of gelatin-rectal capsules which contain the active substance in a mixture with a vegetable oil or paraffin oil.

Liquid preparations for oral administration may be present in the form of syrups or suspensions, e.g., solutions containing from about 0.2% by weight to about 20% by weight of the active substance described, whereby the residue consists of sugar and a mixture of ethanol, water, glycerol and propylene glycol. If desired, such liquid preparations may contain coloring agents, flavoring agents, saccharine and carboxymethylcellulose as a thickening agent.

Solutions for parenteral administration by injection may be prepared as an aqueous solution of a water soluble pharmaceutically acceptable salt of the active compound, preferably in a concentration from about 0.5% by weight to about 10% by weight. These solutions may also contain stabilizing agents and/or buffering agents and may suitably be available in different dosage unit ampoules.

The preparation of pharmaceutical tablets for peroral use is carried out in accordance with the following method:

The solid substances included are ground or sieved to a certain particle size. The binding agent is homogenized and suspended in a certain amount of solvent. The therapeutic compound and necessary auxiliary agents are mixed during a continuous and constant mixing with the binding agent solution and are moistened so that the solution is uniformly divided in the mass without overmoistening any parts. The amount of solvent is usually so adapted that the mass obtains a consistency reminding of wet snow. The moistening of the pulverulent mixture with the binding agent solution causes the particles to gather together slightly to aggregate and the real granulating process is carried out in such a way that the mass is pressed through a sieve in the form of a net of stainless steel having a mesh size of about 1 mm. The mass is then placed in thin layers on a tray to be dried in a drying cabinet. This drying takes place during 10 hours and has to be standardized carefully as the degree of dampness of the granulate is of utmost importance for the following process and for the features of the tablets. Drying in a fluid bed may possibly be used. In this case the mass is not put on a tray but is poured into a container having a net bottom.

After the drying step the granules are sieved so that the particle size wanted is obtained. Under certain circumstances powder had to be removed.

To the so-called final mixture, disintegrating, antifriction agents and antiadhesive agents are added. After this mixture is made the mass should have its correct composition for the tabletting step.

The cleaned tablet punching machine is provided with a certain set of punches and dies, whereupon the suitable adjustment for the weight of the tablets and the degree of compression is tested out. The weight of the tablets is decisive for the size of the dose in each tablet and is calculated starting from the amount of therapeutic agent in the granules. The degree of compression affects the size of the tablet, its strength and its ability to disintegrate in water. Especially as regards the two later properties, the choice of compression pressure (0.5 to 5 ton) calls for something of a balance of conditions. When the right adjustment is set, the preparation of tablets is started, which is carried out with a rate of 20,000 to 200,000 tablets per hour. The pressing of the tablets requires different times and depends on the size of the batch.

The tablets are freed from adhering powder in a specific apparatus and are then stored in closed packages until they are delivered.

Many tablets, especially those which are rough or bitter, are coated with a coating. This means that these are coated with a layer of sugar or some other suitable coating.

The tablets are usually packed by machines having an electronic counting device. The different types of packages include glass or plastic gallipots, and also boxes, tubes and specific dosage adapted packages.

The daily dose of the active substance varies and is dependent on the type of administration, but as a general rule it is 100 to 400 mg/day of active substance for peroral administration and 5 to 20 mg/day for intravenous administration.

The following illustrates the principle and the adaptation of invention without, howver, being limited thereto. Temperature is given in degree Celsius.

EXAMPLE 1

1.9 g of 1,2-epoxy-3-(2-allylphenoxy)-propane and 1.8 g of 4-(2-aminoethoxy)-benzamide were refluxed in 25 ml of isopropanol for 1.5 hours. The reaction mixture was evaporated in vacuo, whereupon the residue was dissolved in acetone and the hydrochloride of 1[2-(4-carbamylphenoxy)-ethylamino]-3-(2-allylphenoxy)-propanol-2 was precipitated by introducing ether containing HCl. Mp. 211° C. The structure was verified with NMR.

EXAMPLE 2

2.8 g of 1,2-epoxy-3-[2-chloro-5-methylphenoxy]propane and 2.7 g of 4-(2-aminoethoxy)-benzamide were refluxed in 25 ml of isopropanol for 5 hours. The mixture was evaporated in vacuo. The residue was dissolved in acetone and the hydrochloride of 1-[2-(4-carbamylphenoxy)ethylamino]-3-(2-chloro-5-methylphenoxy)propanol-2 was precipitated with ether containing HCl. Mp. 250° C. (decomposing). The structure was verified with NMR.

EXAMPLE 3

2.1 g of 1,2-epoxy-3-[4-(2-methoxyethyl)phenoxy]propane and 1.8 g of 4-(2-aminoethoxy)benzamide were reacted with each other in accordance with Example 1. The melting point of 1-[2-(4-carbamylphenoxy)ethylamino]-3-(2-methoxyethyl)phenoxypropanol-2 hydrochloride was 105° C. The structure was verified with NMR.

EXAMPLE 4

0.4 g of 3-(1,2-epoxy-3-propoxy)-4 chlorothiazole and 0.4 g of 4-(2-aminoethoxy)benzamide were reacted in accordance with Example 1. The hydrochloride of 1-[2-(4-carbamylphenoxy)-ethylamino]-3-(4-chloro-2-thiazoloxy)propanol-2 decomposed at 215° C. The structure was verified using NMR.

EXAMPLE 5

1.9 g of 1,2-epoxy-3-(2-allylphenoxy)propane and 2.5 g of 4-(2-aminopropoxy)benzamide were reacted in accordance with Example 1. The hydrochloride of 1-[1-methyl-2-(4-carbamylphenoxy)ethylamino]-3-(2-allylphenoxy)propanol-2 melted at 94° C. The structure was verified using NMR.

EXAMPLE 6

3.8 g of 1,2-epoxy-3-(2-allylphenoxy)propane and 3.3 of 1-(2methylphenoxy)-2-propylamine were reacted in accordance with Example 1. The hydrochloride of 1-[1-methyl-2-(2-methylphenoxy)-ethylamino]-3-(2-allylphenoxy)propanol-2 melted at 142° C. The structure was verified using NMR.

EXAMPLE 7

3.8 g of 1,2-epoxy-3-(2-allylphenoxy)propane and 3.3 of 1-(4-methylphenoxy)-2-propylamine were reacted in accordance with Example 5. The hydrochloride of 1-[1-methyl-2-(4-methylphenoxy)ethylamino]-b 3-(2-allylphenoxy)propanol-2 melted at 146° C. The structure was verified with NMR.

EXAMPLE 8

1.8 g of 1-amino-3-(2-methylisonitrosomethylphenoxy)-propanol-2 and 1.55 g of 4-methylcarbonylmethoxybenzamide were dissolved in 25 ml of methanol and cooled to 0° C. 1.8 g of NaBH$_4$ were then added during ½ hour. 50 ml of water were added and the product was extracted with ethylacetate. The ethylacetate phase is evaporated in vacuo and the substance, 1-[1-methyl-2-(4-carbamoylphenoxy)ethylamino]-3-(2-methylisonitrosomethylphenoxy)propanol-2, is washed with ether and ethylacetate. Mp. 106° C. (HCl).

EXAMPLE 9

In accordance with Example 1 1-[4-(2-(2-methoxycarbonylamino)ethyl)phenoxyethylamino]-3-(2-methylphenoxy)-propanol-2 was prepared from 1,2-epoxy-3-(2-methylphenoxy)propanol-2 was prepared from 1,2-epoxy-3-(2-methylphenoxy)propane and 1-(4-methoxycarbonylaminoethylphenoxy)-2-ethylamine. Mp 93° C. as base.

EXAMPLE 10

1-[2-(4-carbamylphenoxy)ethylamino]-3-(3-allylphenoxy)propanol-2 was prepared in accordance with Example 1 starting from 1,2-epoxy-3-(3-allylphenoxy)propane and 4aminoethoxybenzamide. Mp. 228° C. as hydrochloride.

EXAMPLE 11

1-[2-(4-carbamoylphenoxy)ethylamino]-3-(2-chlorophenoxy)propanol-2 was prepared in accordance with Example 1 starting from 1,2-epoxy-3-(2-chlorophenoxy)propane and 4-aminoethoxy-bensamide. Mp. 228° C. as hydrochloride.

EXAMPLE 12

1-[2-(4-carbamylphenoxy)ethylamino]-3-(2,3-dichlorophenoxy)propanol-2 was prepared in accordance with Example 1 from 1,2-epoxy-3-(2,3-dichlorophenoxy)propane and 4-aminoethoxy-bensamide. Mp. 245° C. as hydrochloride, and 156° C. as base.

EXAMPLE 13

A syrup containing 2% (weight per volume) of active substance was prepared from the following ingredients:

| | |
|---|---|
| 1-[2-(4-carbamylphenoxy)ethylamino]-3-(2-allyl-phenoxy)propanol-2 . HCl | 2.0 g |
| Saccharine | 0.6 g |
| Sugar 1 | 30.0 g |
| Glycerine | 5.0 g |
| Flavoring agent | 0.1 g |
| Ethanol 96% | 10.0 ml |
| Distilled water | ad 100.0 ml |

Sugar, saccharine and the ether salt were dissolved in 60 g of warm water. After cooling, glycerine and a solution of flavoring agents dissolved in ethanol were added. To the mixture water was then added to 100 ml.

The above given active substance may be replaced with other pharmaceutically acceptable acid addition salts.

EXAMPLE 14

1-[2-(4-carbamylphenoxy)ethylamino]-3-(2-chloro-5-methylphenoxy)propanol-2-hydrochloride (250 g) was mixed with lactose (175.8 g), potato starch (169.7 g) and colloidal silicic acid (32 g). The mixture was moistened with a 10% solution of gelatine and was granulated through a 12-mesh sieve. After drying potato starch (160 g), talc (50 g) and magnesium stearate (5 g) were admixed and the mixture thus obtained was pressed into tablets (10 000) which contain 25 mg of substance. The tablets are sold on the market provided with a breaking score to give another dose than 25 mg or to give multiples thereof when broken.

EXAMPLE 15

Granules were prepared from 1-[2-(4-carbamyl-phenoxy) ethylamino]-3-12-(2-methoxyethyl)phenoxy-propanol-2-hydrochloride (250 g), lactose (175.9 g) and an alcoholic solution of polyvinylpyrrolidone (25 g). After drying step the granules were mixed with talc (25 g). potato starch (40 g) and magnesium stearate (2.50 g) and was pressed into 10 000 biconvex tablets. These tablets are primarily coated with a 10% alcoholic solution of shellac and thereupon with an aqueous solution containing saccharose (45%), gum arabicum (5%), gelatine (4%) and dyestuff (0.2%). Talc and powder sugar were used for powdering after the first five coatings. The coating was then coated with a 66% sugar syrup and polished with a 10% carnauba wax solution in carbon tetrachloride.

EXAMPLE 16

1-[2-(4-carbamylphenoxy)ethylamino]-3-(4-chloro-3-thiazoloxy)propanol-2-hydrochloride (1 g), soldium chloride (0.8 g) and assorbic acid (0.1 g) were dissolved in sufficient amount of distilled water to give 100 ml of solution. This solution, which contains 10 mg of active substance on each ml, was used in filling ampoules, which were sterilized by heating at 120° C. for 20 minutes.

BIOLOGICAL EFFECTS

The $\beta$-receptor blocking agents of the present invention were tested as regards their biological properties. All compounds were thereby tested in anesthetized cats (males and females weighing 2.5–3.5 kg) pretreated with reserpine (5 mg/kg body weight administered intra muscularly) about 16 hours before the experiments. The animals were pretreated with reserpine in order to eliminate the endogenous sympathetic control of heart rate and vascular smooth muscle tone. The cats were anaesthetized with pentobarbital (30 mg/kg body weight administered i.p.) and artifically ventilated with room air. A bilateral vagotomy was performed in the neck. Blood pressure was obtained from a cannulated carotid artery and heart rate was registered from a cardiotachometer, triggered by the electrocardiogram. (ECG) Intrinsic beta-mimetic activity on the heart was seen as increased heart rate after drug administration. The test compounds were given intravenously in logarithmically increasing doses. The values obtained were plotted on dose-response curves, from which affinity values ($ED_{50}$) were estimated. At the end of each experiment high doses of isoprenaline were given in order to obtain the maximal heart rate response.

The compounds were also tested on conscious dogs. Beagle dogs were trained to be lying quietly and to be lifted to an erect position by placing their forelegs on a table for 2 minutes. Arterial blood pressure was registered via a blood pressure transducer attached to the dog at the heart level. Heart rate was triggered from the ECG. All dogs were pretreated with methylscopolamine to avoid vagal influences. Recordings were taken before and 15 and 75 min after administration of the test compound, first in supine position for 2 min and then in the erect position for 2 minutes. The test compounds were given in increasing doses with 2 hours intervals.

Table 1 below shows affinity values and intrinsic $\beta$-mimetic activity in reserpinized cats and effects on blood pressure in conscious dogs of compounds of the present invention. Corresponding values for propanolol, (1-isopropylamino-3-(1-naphtoxy)-propanol-2), practolol, (4-(2-hydroxy-3-isopropylaminopropoxy)acetanilide), and metoprolol, (1-isopropylamino-3-[4-(2-methoxyethyl)phenoxy]-propanol-2), are shown for comparison.

Table 1

| | Reserpinized cat | | | Conscious dog | |
|---|---|---|---|---|---|
| | Block of isopren $ED_{50}$ mg/kg | | Intrinsic activity | $\Delta$BP in mm Hg after 1.5 mg/kg i.v. | |
| Compound | HR | PR | beats/min | Supino | Erect |
| Propranolol | 0.1 | 0.1 | 0 | +5 | 0 |
| Practolol | 0.3 | 35 | +15 | | |
| Metroprolol | 0.2 | 4.7 | 0 | −5 | −3 |
| Ex 1 | 0.3 | 1.8 | 0 | −28 | −45 |
| Ex 2 | 0.3 | 4.6 | 0 | | |
| Ex 3 | 1.1 | 8.5 | 0 | | |
| Ex 5 | 0.05 | 0.2 | +15 | −43 | −42 |
| Ex 6 | 0.5 | 0.5 | +24 | | |
| Ex 9 | 0.3 | 2.4 | +40 | | |
| Ex 11 | 0.05 | 1.0 | +16 | −28 | −20 |
| Ex 17 | 0.1 | 1.5 | +8 | −23 | −46 |
| Ex 18 | 0.04 | 0.3 | +13 | | |
| Ex 19 | 1.7 | <8.5 | 0 | | |
| Ex 20 | 0.03 | <8.5 | + | | |

The experiments demonstrate that the compounds tested are potent $\beta$-receptor antagonists with or without intrinsic $\beta$-mimetic activity. The compounds also decrease blood pressure in conscious dogs significantly more than propranolol, practolol and metoprolol.

The following compounds have further been prepared:

$$ArOCH_2CHOHCH_2NH-\overset{R^5}{\underset{|}{CH}}(CH_2)_nO-\underset{R^2}{\overset{R^1}{\diagdown N \diagup}}-(CH_2)_mR^9$$

| Example | Ar | $R^1$ | $R^2$ | $R^5$ | n | m | $R^9$ | Mp. °C. | |
|---|---|---|---|---|---|---|---|---|---|
| 17 | Phenyl | 2-$CH_2$=CH—$CH_2$O— | H | H | 1 | 0 | 4-$NH_2$CO— | 136–7 | (HCl) |
| 18 | " | 2-CH≡C—$CH_2$O— | H | H | 1 | 0 | 4-$NH_2$CO— | 215 | (HCl) |
| 19 | " | 2-$NH_2$COCH_2— | H | H | 1 | 0 | 4-$NH_2$CO— | 176 | (HCl) |
| 20 | " | 2-HOCH_2CH_2NHCOCH_2O | H | H | 1 | 0 | 4-$NH_2$CO— | 66 | (p-OH—bensoate) |
| 21 | " | 2-$CH_2$=CH—$CH_2$O— | H | H | 2 | 0 | 4-$NH_2$CO— | 200 | (HCl) |
| 22 | " | 2-$CH_2$=CH—$CH_2$O | H | H | 4 | 0 | 4-$NH_2$CO— | oil | (HCl) |
| 23 | 1,2,5-thiadiazolyl | | 4-Cl | H | 1 | 0 | 4-$NH_2$CO | >250 | (HCl) |

We claim:

1. A method for treating cardiovascular diseases comprising administering to mammals suffering therefrom a therapeutically effective amount of $\beta$ receptor blocking agent of the general formula

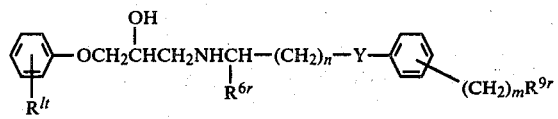

wherein $R^{1t}$ is selected from the group consisting of —OCH$_2$CONHCH$_2$CH$_2$OH and —OCH$_2$CONHCH$_2$CH$_2$OCH$_3$;

$R^{6r}$ is selected from the group consisting of hydrogen and alkyl;

$R^{9r}$ is selected from the group consisting of hydrogen and —CONH$_2$;

Y is a divalent member selected from the group consisting of O and —CH$_2$—;

n is an integer from 0 to 5 inclusive;

m is an integer from 0 to 2 inclusive;

when $R^{9r}$ is hydrogen, m being at least 1; when Y is —CH$_2$—, n is 1 or 2; and alkyl and alkoxy groups, when present, have from 1 to 7 carbon atoms; or a pharmaceutically acceptable salt thereof.

2. A method according to claim 1 wherein said compound is selected from the group consisting of 1-[2-(4-carbamylphenoxy)ethylamino]-3-[2-(ω-hydroxyethylaminocarbonylmethoxy)phenoxy]-propanol-2, and 1-[2-(4-carbamylphenoxy)ethylamino]-3-[2-(ω-methoxyethylaminocarbonylmethoxy)phenoxy]-propanol-2, or a pharmaceutically acceptable salt thereof.

3. A compound of the formula

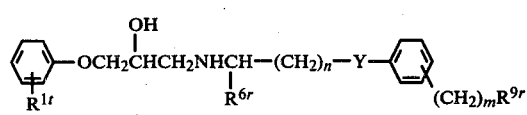

wherein $R^{1t}$ is selected from the group consisting of —OCH$_2$CONHCH$_2$CH$_2$OH and —OCH$_2$CONHCH$_2$CH$_2$OCH$_3$;

$R^{6r}$ is selected from the group consisting of hydrogen and alkyl;

$R^{9r}$ is selected from the group consisting of hydrogen and —CONH$_2$;

Y is a divalent member selected from the group consisting of O and —CH$_2$—;

n is an integer from 0 to 5 inclusive;

m is an integer from 0 to 2 inclusive;

when $R^{9r}$ is hydrogen, m being at least 1; when Y is —CH$_2$—; n is 1 or 2; and alkyl and alkoxy groups, when present, have from 1 to 7 carbon atoms; or a pharmaceutically acceptable salt thereof.

4. A compound according to claim 3 selected from the group consisting of

1-[2-(4-carbamylphenoxy)ethylamino]-3-[2-(ω-hydroxyethylaminocarbonylmethoxy)phenoxy]-propanol-2, and 1-[2-(4-carbamylphenoxy)ethylamino]-3-[2-(ω-methoxyethylaminocarbonylmethoxy)phenoxy]-propanol-2, or a pharmaceutically acceptable salt thereof.

5. A pharmaceutical preparation for the treatment of cardiovascular diseases by blockage of the adrenergic β receptors of a mammal comprising a dosage unit in an amount effective to provide a blockade of the adrenergic β receptors of a compound of the formula

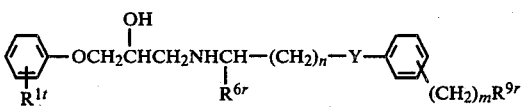

wherein $R^{1t}$ is selected from the group consisting of —OCH$_2$CONHCH$_2$CH$_2$OH and —OCH$_2$CONHCH$_2$CH$_2$OCH$_3$;

$R^{6r}$ is selected from the group consisting of hydrogen and alkyl;

$R^{9r}$ is selected from the group consisting of hydrogen and —CONH$_2$;

Y is a divalent member selected from the group consisting of O and —CH$_2$—;

n is an integer from 0 to 5 inclusive;

m is an integer from 0 to 2 inclusive;

when $R^{9r}$ is hydrogen, m being at least 1, when Y is —CH$_2$—, n is 1 or 2; and alkyl and alkoxy groups, when present, have from 1 to 7 carbon atoms; or a pharmaceutically acceptable salt thereof, together with a pharmaceutically acceptable carrier therefor.

6. A pharmaceutical preparation according to claim 5 wherein said compound is selected from the group consisting of 1-[2-(4-carbamylphenoxy)ethylamino]-3-[2-(ω-hydroxyethylaminocarbonylmethoxy)phenoxy]-propanol-2, and 1-[2-(4-carbamylphenoxy)ethylamino]-3-[2-(ω-methoxyethylaminocarbonylmethoxy)phenoxy]-propanol-2, or a pharmaceutically acceptable salt thereof, together with a therapeutically acceptable carrier therefor.

* * * * *